(12) United States Patent  
Iyengar et al.

(10) Patent No.: US 8,877,033 B2  
(45) Date of Patent: Nov. 4, 2014

(54) METHOD AND APPARATUS FOR ASSAY OF ELECTROCHEMICAL PROPERTIES

(71) Applicant: AgaMatrix, Inc., Salem, NH (US)

(72) Inventors: Sridhar G. Iyengar, Salem, NH (US); Ian Harding, Wells (GB)

(73) Assignee: AgaMatrix, Inc., Salem, NH (US)

( * ) Notice: Subject to any disclaimer, the term of this patent is extended or adjusted under 35 U.S.C. 154(b) by 0 days.

(21) Appl. No.: 13/970,117

(22) Filed: Aug. 19, 2013

(65) Prior Publication Data

US 2014/0048425 A1    Feb. 20, 2014

Related U.S. Application Data

(63) Continuation of application No. 13/356,827, filed on Jan. 24, 2012, now Pat. No. 8,512,546, which is a (Continued)

(51) Int. Cl.
*G01N 27/327* (2006.01)
*A61B 5/1486* (2006.01)
*A61B 5/1495* (2006.01)
*C12Q 1/00* (2006.01)
*A61B 5/145* (2006.01)
*G01N 27/416* (2006.01)

(52) U.S. Cl.
CPC .......... *G01N 27/4168* (2013.01); *A61B 5/1486* (2013.01); *A61B 5/1495* (2013.01); *C12Q 1/004* (2013.01); *A61B 5/14532* (2013.01); *C12Q 1/006* (2013.01); *C12Q 1/001* (2013.01)
USPC ........ 205/775; 205/777.5; 205/792; 204/400; 204/406; 204/403.01

(58) Field of Classification Search
USPC ............... 205/775, 777.5, 792; 204/400, 406, 204/403.01–403.15
See application file for complete search history.

(56) References Cited

U.S. PATENT DOCUMENTS 940,316 A    11/1909   Hoyt
4,096,047 A   6/1978   Hale et al.

(Continued)

FOREIGN PATENT DOCUMENTS

DE    4100727 A1    7/1992
DE    4300499 A1    7/1994

(Continued)

OTHER PUBLICATIONS

Therasense, Inc., Form 10-K for Fiscal year ended Dec. 31, 2002.

(Continued)

*Primary Examiner* — Alex Noguerola
(74) *Attorney, Agent, or Firm* — Larson & Anderson, LLC

(57) ABSTRACT

The presence of a select analyte in the sample is evaluated in an electrochemical system using a conduction cell-type apparatus. A potential or current is generated between the two electrodes of the cell sufficient to bring about oxidation or reduction of the analyte or of a mediator in an analyte-detection redox system, thereby forming a chemical potential gradient of the analyte or mediator between the two electrodes After the gradient is established, the applied potential or current is discontinued and an analyte-independent signal is obtained from the relaxation of the chemical potential gradient. The analyte-independent signal is used to correct the analyte-dependent signal obtained during application of the potential or current. This correction allows an improved measurement of analyte concentration because it corrects for device-specific and test specific factors such as transport (mobility) of analyte and/or mediator, effective electrode area, and electrode spacing (and as a result, sample volume), without need for separate calibration values. The analysis can be performed using disposable test strips in a hand held meter, for example for glucose testing.

20 Claims, 22 Drawing Sheets

Related U.S. Application Data continuation of application No. 12/398,321, filed on Mar. 5, 2009, now Pat. No. 8,123,920, which is a continuation of application No. 10/924,510, filed on Aug. 23, 2004, now Pat. No. 7,501,052.

(60) Provisional application No. 60/529,648, filed on Dec. 15, 2003, provisional application No. 60/496,787, filed on Aug. 21, 2003.

(56) References Cited

U.S. PATENT DOCUMENTS

| | | | |
|---|---|---|---|
| 4,340,458 | A | 7/1982 | Lerner et al. |
| 4,449,089 | A | 5/1984 | Winkler |
| 5,256,961 | A | 10/1993 | Henkelmann |
| 5,438,271 | A | 8/1995 | White et al. |
| 5,567,302 | A | 10/1996 | Song et al. |
| 5,644,501 | A | 7/1997 | Lin et al. |
| 5,942,102 | A | 8/1999 | Hodges et al. |
| 6,179,979 | B1 | 1/2001 | Hodges et al. |
| 6,251,260 | B1 | 6/2001 | Heller et al. |
| 6,284,125 | B1 | 9/2001 | Hodges et al. |
| 6,645,368 | B1 | 11/2003 | Beaty et al. |
| 6,652,720 | B1 | 11/2003 | Mansouri et al. |
| 6,749,740 | B2 | 6/2004 | Liamos et al. |
| 6,783,645 | B2 | 8/2004 | Cheng et al. |
| 6,821,401 | B2 | 11/2004 | Diehl |
| 6,833,683 | B2 | 12/2004 | Winkler |
| 6,921,475 | B2 | 7/2005 | Kuhr et al. |
| 7,347,926 | B2 | 3/2008 | Morita et al. |
| 7,501,052 | B2 | 3/2009 | Iyengar et al. |
| 2005/0067301 | A1 | 3/2005 | Morita et al. |
| 2005/0258034 | A1 | 11/2005 | Iketaki et al. |
| 2010/0126856 | A1 | 5/2010 | Wang et al. |

FOREIGN PATENT DOCUMENTS

| | | |
|---|---|---|
| EP | 0269794 A2 | 6/1988 |
| WO | 03306285 A1 | 5/2003 |
| WO | 03060154 A2 | 7/2003 |
| WO | 03069304 A2 | 8/2003 |

OTHER PUBLICATIONS

McDuffie, et al., Twin-Electrode Thin-Layer Electrochemistry, Analytical Chemistry, Jun. 1966, pp. 883-890, vol. 38, No. 7.

Atkins, P., Physical Chemistry, 1999, pp. 737-749, Publisher: 6th ed. Freeman, New York.

Crow, D. R., Chapter 4: The conducting properties of electrolytes, Principles and Applications of Electrochemistry, 1998, pp. 43-67, Publisher: 4th ed. Stanley Thornes Publishers, Cheltenham, UK.

Macinnes, Chapter 3: Electrolytic Conductance and the "Classical" theories of Dissociation, The principles of Electrochemistry, 1939, pp. 40-58, Chapter 3, Publisher: Reinhold Publishing Corp., New York.

Schmidt-Weinmer, Ueber die Polarisation einer symmetrischen Redoxzelle mit kleinem Electrodenabstand: Eine Methods zur Bestimmung der lo, 1967, pp. 91-101, vol. 71, No. 1; Published in: DE.

Romero et al., Regression models for the determination of the absorbed dose rate with an extrapolation chamber for flat ophthamic applicators, 1995, pp. 234-252, vol. 68, No. 2, Publisher: Health Physics Society.

Vallet et al., Steady-State Composition Profiles in Mixed Molten Salt Electrochemical Devices, Journal of the Electrochemical Society, Aug. 1978, pp. 1193-1198, vol. 125, No. 8.

Macinnes, Chapter 4: Electrical Transference, The principles of Electrochemistry, 1939, pp. 59-95, Chapter 4, Publisher: Reinhold Publishing Corp., New York.

Macinnes, Chapter 20; Conductance Methods, The principles of Electrochemistry, 1939, p. 382, Publisher: Reinhold Publishing Corp., New York.

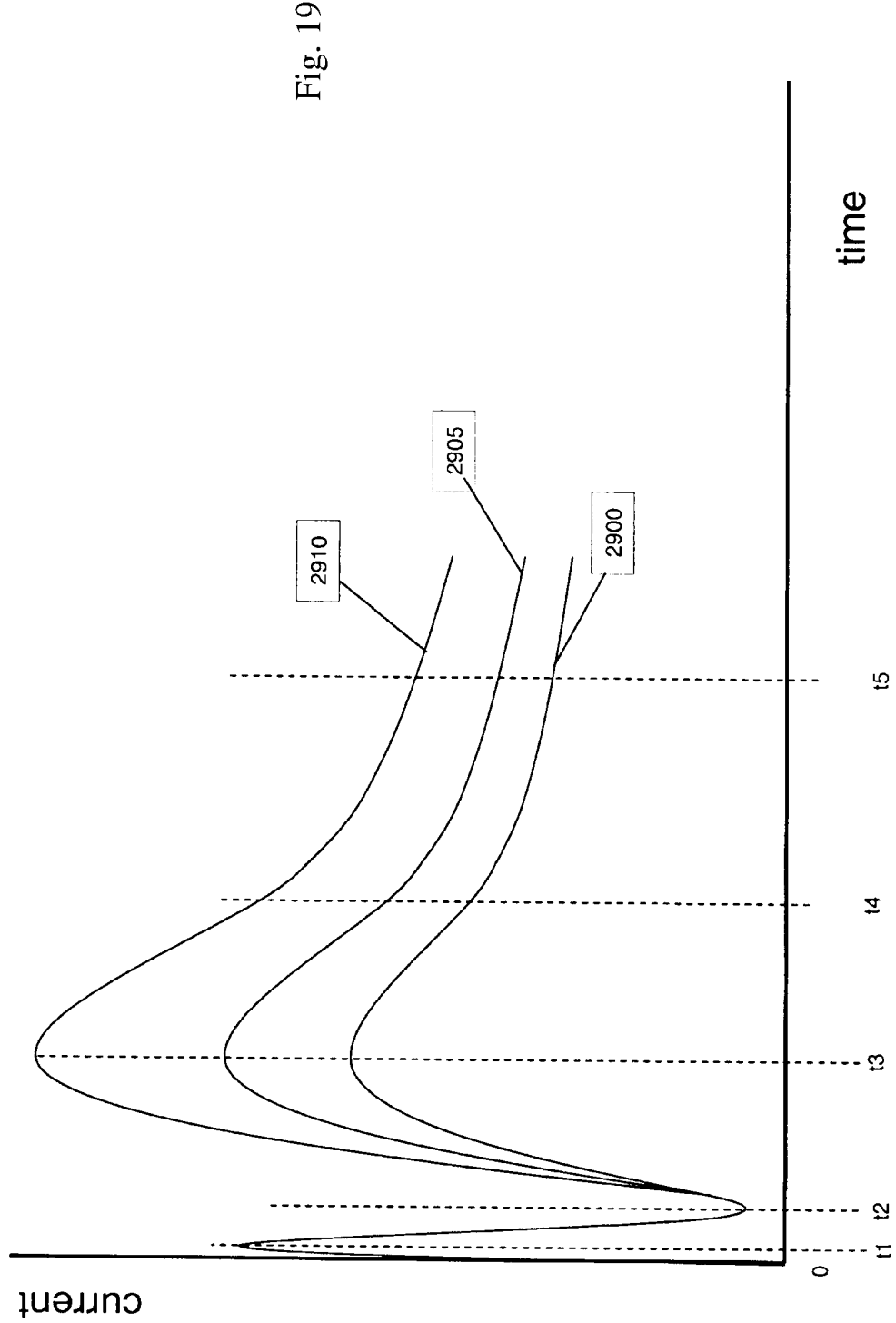

METHOD AND APPARATUS FOR ASSAY OF ELECTROCHEMICAL PROPERTIES

This application claims the benefit of U.S. Provisional Applications 60/496,787 filed Aug. 21, 2003 and 60/529,648, filed Dec. 15, 2003, both of which application are incorporated herein by reference.

BACKGROUND OF THE INVENTION

This application relates to methods and apparatus for assay of electrochemical properties, and in particular to methods and apparatus for the determination of analytes, for example glucose, from small volume samples.

Electrochemical means to quantify or detect an analyte have often been chosen because of their simplicity, both in terms of device manufacture and in terms of ease of use. Electrochemical sensors have often been in the form of either potentiometric or amperometric devices. Potentiometric devices measure the effects of the charges on atoms and their positions; examples include the chemFET (chemical field effect transistor) and the ion-selective electrode (including pH electrodes). Amperometric devices operate on the principle of applying a potential and measuring the resulting current, where the magnitude of the current generated is usually related to the amount of analyte present; alternatively, the total charge passed over a time may be used to represent the amount of analyte in a region of the sample. Because the range of compounds that can generate electrochemical currents is smaller than those that carry charges, amperometric devices can often offer greater selectivity. Much effort has therefore been concentrated in amperometric sensors in fields as diverse as environmental monitoring and medicine.

A demand for ever-increasing numbers of measurements on ever-smaller samples at a lower cost has meant that amperometric sensors are reaching a natural limit. An old form of amperometric analysis was to use a conduction cell, where the movement of species from one electrode to another through the sample was related to its concentration. This approach required careful cell-to-cell calibration to correct for variations in electrode area and separation, which were expressed as a single cell constant for correction of the cell reading. In more recent forms of amperometric analysis, taking readings rapidly meant only species near the investigated electrode had an effect on the result. However, with present trends towards increasingly smaller samples, the effects of reaction at one electrode are rapidly felt as undesired interference at another electrode, and even if this effect can be removed (for example by use of a silver/silver chloride cathode), the small sample size also means the small amount of current passed will be more difficult to measure accurately. Furthermore, the readings from miniature, disposable devices are made uncertain because of the limits of manufacturing tolerance. Thus, a method and apparatus for performing the electrochemical assay in a miniature conduction cell that would be able to produce its own correction factors for manufacturing, environmental and sample variations would be useful and beneficial.

SUMMARY OF THE INVENTION

The present invention relates to a method for evaluating a sample for the presence of a select analyte in the sample in an electrochemical system using a conduction-cell type apparatus. The method comprises the steps of (a) introducing the sample into a space between two electrodes of a conduction cell;

(b) applying a potential or current between the two electrodes sufficient to bring about oxidation or reduction of the analyte or of a mediator in an analyte-detection redox system, thereby forming a chemical potential gradient of the analyte or mediator between the two electrodes;

(c) after the gradient is established, discontinuing the applied potential or current and obtaining an analyte-independent signal reflecting relaxation of the chemical potential gradient;

(d) optionally applying a potential or current between the electrodes after the analyte-independent signal is obtained;

(e) obtaining an analyte-dependent signal during the application of the potential or current in step (b) or step (d) or both, and (f) correcting the analyte-dependent signal obtained in step (e) using the analyte-independent signal obtained in step (c) to obtain a corrected analyte-dependent signal indicative of the presence of the selected analyte in the sample.

The use of the two signals, the analyte-independent signal and the anlyte-dependent signal, allows an improved measurement of analyte concentration over the conventional usage of an analyte-dependent signal alone because the analyte-independent signal provides information about device-specific and test specific factors such as transport (mobility) of analyte and/or mediator, effective electrode area, and electrode spacing (and as a result, sample volume), without need for separate calibration values. This means that using the method and apparatus of the invention auto-calibration can be achieved that improves the accuracy and precision of the measurement without increasing the cost.

The present invention also provides an apparatus for use in practicing the method of the invention. The apparatus comprises a housing in which electronics effective to generate and observe the first and second signals are housed. In preferred embodiments, the housing is of a size that can be hand-held, and has an opening for receiving a disposable single use test strip of the type now known for testing of blood glucose.

BRIEF DESCRIPTION OF THE DRAWINGS

FIG. 19 illustrates in schematic form examples amperometric signals for a transient system.

DETAILED DESCRIPTION OF THE INVENTION

Definitions

Figure 1:
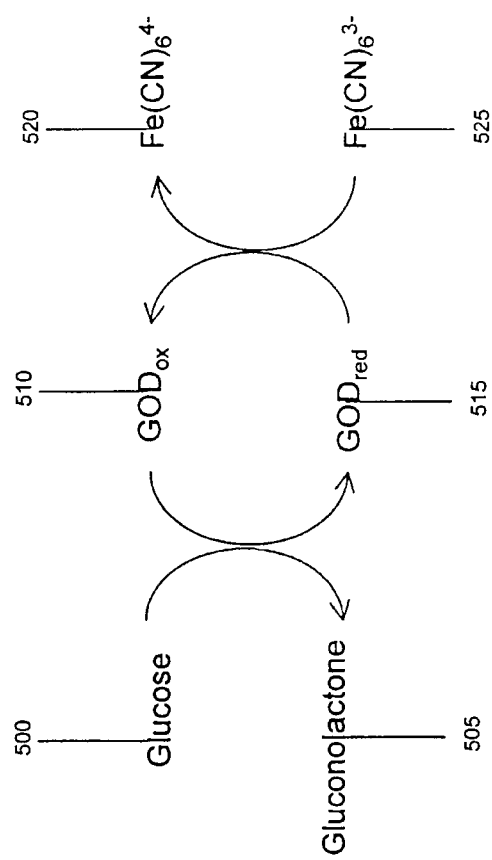
FIG. 1 shows the reactions of an exemplary analyte-detection system for analysis of glucose.

As used herein, the term "analyte" refers to a chemical or biological species that an experiment or device is intended to detect and/or measure.

As used herein, the term "interferent" refers to a chemical or biological species that is an interfering agent in the analysis of the analyte, that is present in the sample and that contributes error to the detection or measurement.

As used herein, the term "autocorrection" refers to a process where information obtained about an apparatus during the course of use of that apparatus is applied to other forms of information from the apparatus obtained during the course of use of that apparatus to improve the accuracy of all or parts of the information.

As used herein, the term "conduction cell" refers to a device comprising two electrodes in contact with a solution, such that the conductance of the solution can be calculated by passing current between the electrodes.

As used herein, the term "conductivity cell" refers to a conduction cell.

As used herein, the term "sample factors" refers to properties and/or factors relating to the sample solution from which an electrochemical signal is recorded to measure certain properties of that sample solution. Examples include, but are not limited to, specific analyte concentration, interferent concentrations, viscosity of the solution, dielectric of the sample, and particulate loading of the sample.

As used herein, the term "apparatus factors" refers to properties and/or factors relating to the apparatus used to measure the electrochemical signal relating to the sample solution. Examples include, but are not limited to, electrode geometry, electrode dimensions, and protective layers in the apparatus, which could include polymer meshes or coatings.

As used herein, the term "potentiometric relaxation" refers to change in potential with time. An example of potentiometric relaxation includes the change in potential between two electrodes when an applied potential has been removed and substantially zero current flows between the electrodes. This change in potential can be a result of changes in the concentration profiles of a reduced chemical species and an oxidized chemical species in a sample with which the two electrodes are in electrolytic contact.

As used herein, the term "environmental factors" refers to properties and/or factors other than "sample factors" or "apparatus factors". Examples include, but are not limited to, temperature, humidity, physical vibrations, and ambient radio waves.

As used herein, the term "effective electrode area" refers to the electrode area that is in electrolytic contact with the sample. The effective electrode area may be varied by altering the geometry of the electrode or by partial contact of the electrode to the sample.

As used herein, the term "electrolytic contact" refers to having an electrochemical system comprised of at least one electrode deployed in a manner so as to gather electrochemical information from a sample. Examples include, but are not limited to, an electrode in physical contact with a sample; an electrode separated from a sample by a membrane, a film, or other material; and an electrode separated from a sample by an aqueous medium. Examples of electrochemical information include Faradaic current, nonfaradaic current, and chemical potential.

As used herein, the term "steady state" refers to a condition in which some specified characteristic of a condition, such as but not limited to a value, rate, periodicity, or amplitude, exhibits only negligible change over an arbitrarily long period of time. This phrase also includes a condition that exists after all or nearly all initial transients or fluctuating conditions have damped out, and all currents, voltages, or fields remain substantially constant, or oscillate uniformly or substantially uniformly. This phrase also includes conditions that have nearly reached steady state. The term "steady-state" refers to "steady state".

As used herein, the term "RAC" refers to redox-active compound. These are substances that can participate in oxidation-reduction reactions. Examples of RACs include ferricyanide, ferrocyanide, ferrocene, oxygen, and hydrogen peroxide. It will be appreciated that the identification of a species as a redox active compound is dependent on the electrochemical cell, and the potential differences in the cell, such that a given compound may be an RAC in one use and non-redox active in some other environment.

As used herein, the term "NRAC" refers to substances that are not RACs.

The term "mediator in an analyte-detection redox system" refers to an electrochemical signal source which is not itself an analyte but which is an RAC. The "analyte-detection redox system" is a system that permits the electrochemical detection of an NRAC-analyte. By way of example, an analyte-detection redox system for the detection of glucose comprises an enzyme such as glucose oxidase that is capable of oxidizing glucose, and an RAC-mediator that is capable of reoxidizing enzyme to restore is to active form. FIG. 1 shows the reaction involved in an analyte-detection redox system for the detection of glucose.

As used herein, the term "stimulus waveform" refers to a voltage or current that is applied to the electrochemical sensor system, which can be time-varying, not time-varying, AC, and/or DC.

As used herein, the phrase "evaluating a sample for the presence of a select analyte" encompasses both qualitative detection of the presence of the analyte, that is whether or not the analyte is present in detectable amounts in the sample, semiquantitative detection, that is whether or not the analyte is present in an amount greater than a predetermined threshold value, and quantitative evaluation, that is determination of the actual numerical amount of the analyte that is present.

The term "analyte-dependent signal" refers to an observed electrochemical signal, which may be in the form of a current or changing potential the magnitude of which is dependent on the presence or amount of the analyte. An analyte-dependent signal need not be solely dependent on the presence or amount of analyte, and indeed the uncorrected signal discussed in this application is generally dependent on other factors besides the presence and/or amount of analyte.

The term "analyte-independent signal" refers to a signal whose time-domain characteristics are dependent on factors other than the amount of analyte. It will be appreciated that the existence of the analyte-independent signal is dependent on the presence of analyte, but that the rate of decay of the signal, i.e. the time-domain characteristics, do not depend on analyte concentration, at least over the range of concentrations encountered in ordinary measurements.

Method of the Invention

In accordance with a first aspect of the invention, there is provided a method of evaluating a sample for the presence of a select analyte. The method includes the step of applying to the electrochemical system a potential or current sufficient to bring about oxidation or reduction of the analyte, or of a mediator in an analyte-detection redox system. This application of potential or current results in the formation of a chemical potential gradient of the analyte or mediator across the space between the two electrodes.

After the gradient is established, the applied potential or current is discontinued, leaving a device in which analyte or mediator in reduced and oxidized forms is distributed in concentration gradients between the electrodes. This gradient establishes a potential difference between the electrodes, and in the absence of an applied potential or current, the gradients and the associated potential difference relax to an equilibrium state of even distribution. The time course of this relaxation can be monitored by monitoring the potential difference. The time course of the relaxation is dependent on factors such as effective electrode area, temperature, electrode spacing, hematocrit, but is substantially independent of the concentration of analyte.

After the potential decay is monitored, an external potential is optionally again applied to the system. An uncorrected analyte-dependent signal is obtained from monitoring the system during either the first application of potential, the second application of potential or both. Additional cycles of potential on and off could be used, and the measurements could be made at any one or any combination of these cycles. The uncorrected analyte-dependent signal is generally a signal that is capable of providing, on its own, an indication of the presence of the analyte. In preferred embodiments of the invention, the potential is applied and the analyte-dependent signal is a current signal derived from amperometric evaluation of the analyte. The analyte-dependent signal may also be a potential difference that results from maintaining a desired current between the electrodes. Thus, the analyte-dependent signal comprises a signal component that is dependent on the presence/concentration of the select analyte, and may also comprise components that depend on other factors, including sample factors, environmental factors and apparatus factors that are not dependent on the presence or concentration of the selected analyte.

To provide a more accurate assessment of the analyte, it is desirable to correct the original analyte-dependent signal for these analyte-independent factors, and that is the purpose of the present invention. Thus, the final step of the invention is the correction of the uncorrected analyte-dependent signal based on the observed analyte-independent potential decay to form a corrected analyte-dependent signal. This signal is then preferably converted into a user-friendly output, for example in the form of a visible display indicating the presence or concentration of analyte in the sample.

The potential applied to the system to generate the gradient and in the optional post-gradient-relaxation potential application step may be a time-invariant or a time-varying potential. PCT Publications WO 03/060154 and WO 03/069304, which are incorporated herein by reference, each describe the usage of time-varying potentials to generate an analyte-dependent signal.

Figure 2:
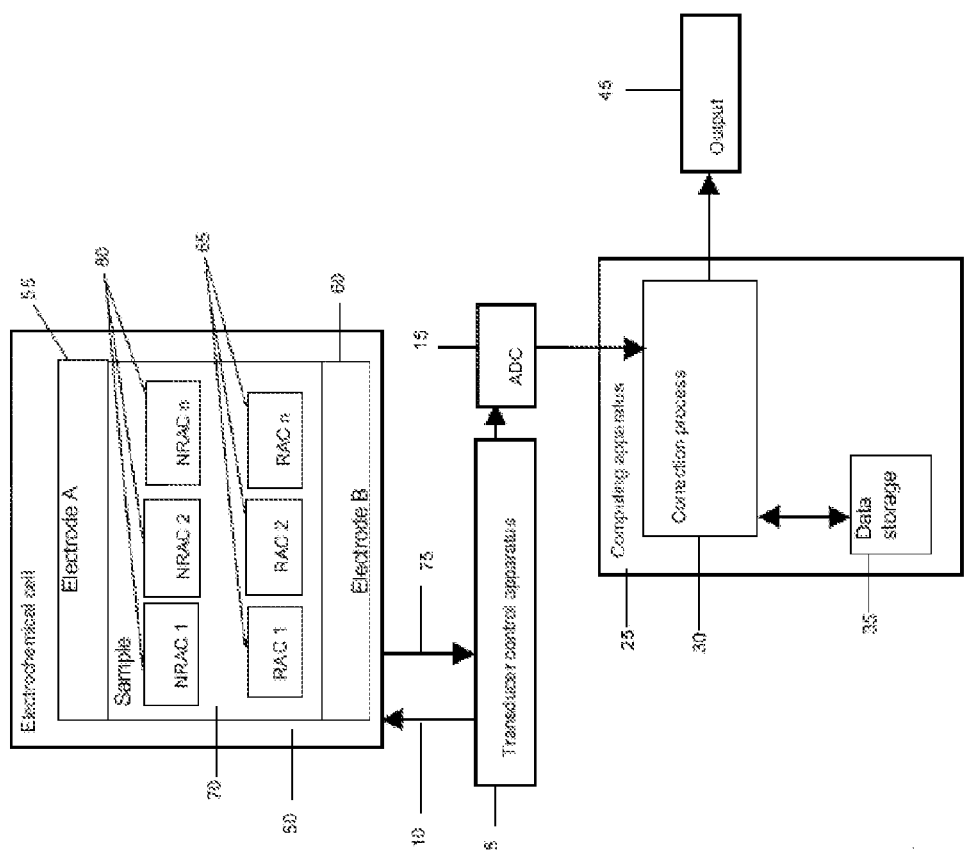
FIG. 2 shows an embodiment of the invention.

FIG. 2 illustrates an embodiment of the invention, in which correction is made for measurement variations that may arise in a conductance-cell electrochemical sensor from sources other than analyte concentration. All arrows represent a set of communication channels, unless otherwise labeled, and can include but are not limited to, electrical transmission via physical conductors, wireless transmission, and multiple channels of communication.

As shown in FIG. 2, a transducer control apparatus (TCA) 5 applies a stimulus waveform signal 10 to an electrochemical cell 50. The electrochemical cell 50 is based on a conduction cell and is comprised of at least two electrodes, indicated by electrode A 55 and electrode B 60. The sample 70 is in electrolytic contact with at least electrode A 55 and electrode B 60 and is comprised of redox active compounds 65 and non-redox active compounds 80. The TCA 5 has means of potentiostat and galvanostat operation and can switch between the two modes as needed. In potentiostatic operation, a potential is applied and a current is generated. The potential is determined based on the redox properties of the analyte or mediator to be oxidized/reduced at the electrodes. In galvanostat operation, a current is applied and a potential is generated.

The stimulus waveform signal 10 causes an electrochemical signal 75 to be generated at each of the electrodes, indicated by electrode A 55 and electrode B 60 by at least one of the RACs 65 and/or at least one of the NRACs 80 in the sample 70. The signal 10 may be a current signal or a potential signal. The signal 10 may be substantially zero amps, substantially not zero amps, substantially zero volts, and/or substantially not zero volts. This response signal 75 is detected and measured by the transducer control apparatus 5. The signal 75 may be a current signal or a potential signal.

To facilitate digital processing of the stimulus waveform signal 10 and the response signal 75, an analog-to-digital converter (ADC) 15 may be used to convert analog signals into a digital signal. An anti-aliasing filter may be used in conjunction with the ADC to filter and the signal is filtered before digitizing. One of ordinary skill in the art will recognize the possibility that such a filter may be part of the ADC itself.

A computing apparatus 25 receives the digitized signal from the ADC 15 for processing. The computing apparatus is programmed to execute a correction process 30, and includes data storage 35, for example in the form of a data storage disk, optical disk, or writable memory which can store both program commands, reference data and results.

The correction process 30 uses functions and/or equations stored in the data storage 35 to modify signal to correct for variations in the signal that may arise from sources other than analyte concentration and compute useful derived quantities. One example of a useful derived quantity is the concentration of the desired analyte in the sample. The correction process 30 can also make use of calibration data that may be contained in data storage 35.

The derived quantities are then sent to an output 45 in a useful manner. Examples of a useful manner of output are having the concentration of the analyte displayed to the user in a visual display or having the concentration of the analyte transmitted and stored by electronic means. In the case of a purely qualitative determination, the useful output can be in the form of a binary display such as a Yes/No, red/green on/off condition in a lighted display, or audible signal.

In one embodiment of the invention, a potential is applied between the electrodes of the cell, and current generated as a result of this applied potential is measured as the analyte-dependent signal. The potential can be applied until a steady state current is reached, and the current is then measured. Alternatively, the current can be measured on a current transient, before steady state is reached.

When the measurement is being taken in the method of the invention, a sample is located between two electrodes and comprises an electrochemically active species in both oxidized and reduced forms. One of these forms is at a concentration related to the amount of an analyte of interest. The other form is in excess. A potential difference is applied between the electrodes that causes oxidation of the reduced form at one electrode and reduction of the oxidized form at the other. This generates (i) a difference in chemical potentials in the solution environments near the two electrodes; and (ii) an electric current in the circuitry that connects the two electrodes.

The difference in chemical potentials creates a concentration gradient of both forms of the electrochemically active species that encourages diffusion. By maintaining a steady difference in chemical potentials, the diffusion can reach a steady state and the electric current can reach a steady level.

Removing electrical communication between the two electrodes prevents maintenance of the concentration gradients, which begins to weaken because of diffusion. The weakening of the concentration gradients results in changes in the chemical potentials near each electrode. The changes can be monitored by measuring the potential difference between the two electrodes. The magnitude of the measured electric current that flowed between the two electrodes on application of a steady potential is found to be substantially dependent on the analyte concentration and substantially dependent on the mobility of the electrochemically active species. The changes in potential between the electrodes upon electrically isolating them are found to be substantially dependent on the mobility, but not substantially dependent on the analyte concentration. A measure of analyte concentration that is substantially independent of mobility can be derived by suitable combination of these two.

A suitable chemical potential difference can be generated by application of a steady potential or a potential that may vary without substantially destabilizing the chemical potential, either to maintain a stable current (e.g. chronopotentiometry) or to stimulate other aspects of the system (e.g. ac impedance spectroscopy.)

An adequate perturbation of chemical potentials may be generated by application of an electric potential so that the change in chemical potentials may be monitored by subsequent electrical isolation of the electrodes, without ever reaching a steady state in the electric current. In this case, a transient current is measured that is substantially dependent on analyte concentration and the mobility of the electrochemically active species. The changes in potential between the electrodes upon electrically isolating them are again found to be substantially dependent on the mobility, but not substantially dependent on the analyte concentration. A measure of analyte concentration that is substantially independent of mobility can therefore again be derived by suitable combination of these two. Whilst the form of the interdependence may vary from the steady state case, the ability to remove the mobility dependence is maintained.

In another embodiment of the invention, a current is applied between the electrodes of the cell, and potential difference generated as a result of this applied potential is measured as the analyte-dependent signal. The current can be applied until a steady state potential is reached, and the potential difference is then measured. Alternatively, the potential difference can be measured on a potential transient, before steady state is reached.

In these example embodiments, the electrochemical cell design, stimulus waveforms, and signal analysis processes are designed to improve the measurement performed by a conductance-cell sensor system to reduce errors from variations other than the concentration of the desired analyte.

The use of a conductance cell to measure concentration and transport properties of chemical substances had been previously described (MacInnes, 1939). In the particular case of a charged species, such as an ion, there are typically four factors that contribute to the transport properties of the species (Crow, 1998): concentration gradients, potential gradients, temperature gradients, convection (e.g. by mechanical stirring). For the case of an electrochemical sensor system, it is generally assumed that concentration gradients and potential gradients are the factors that contribute significantly to the transport properties. Furthermore, Schmidt-Weinmar (1967) indicates that convection effects can be effectively eliminated from conductance-cell systems by placing the electrodes less than 200 microns apart, and preferably less than 150 microns apart.

Figure 3:
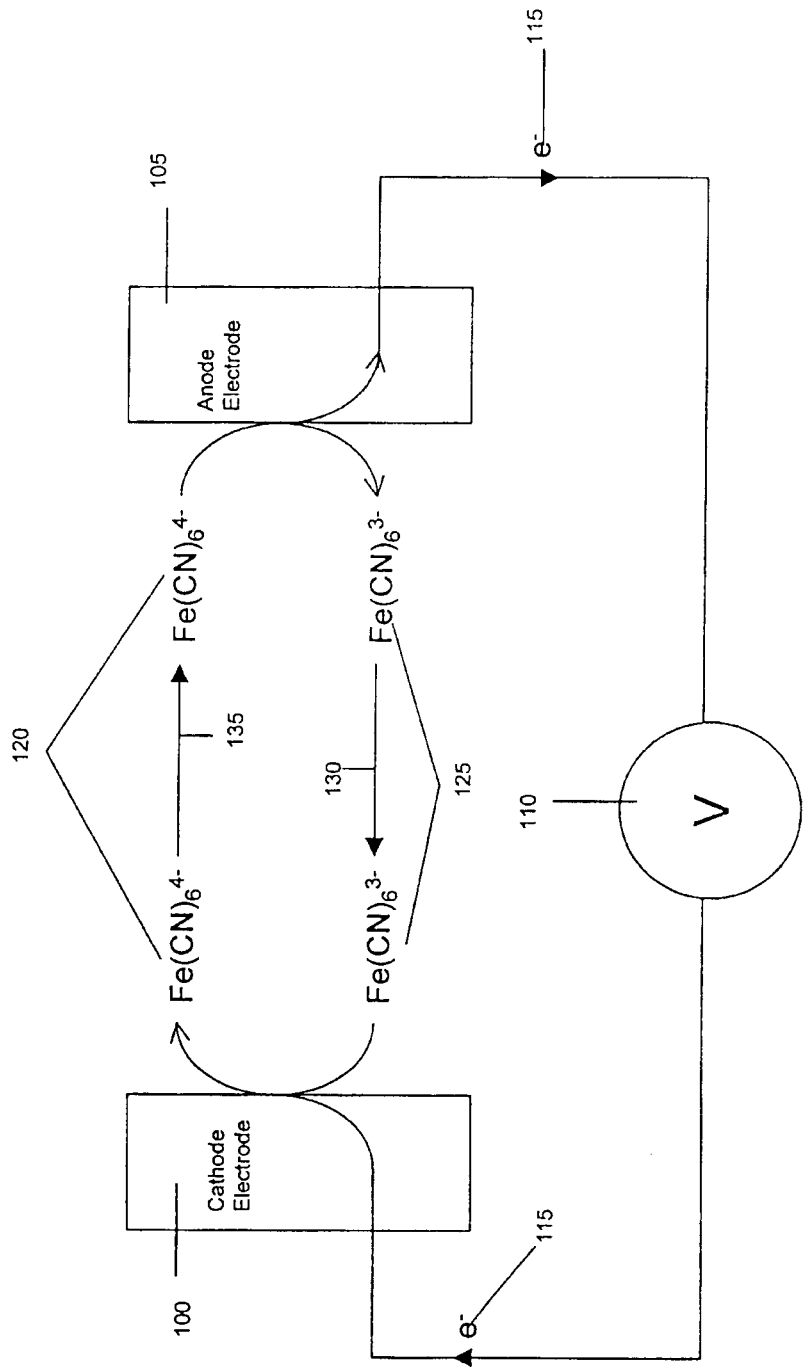
FIG. 3 illustrates the general operation of a conductance cell.

FIG. 3 illustrates one general principle of a conventional conductance cell. The figure references a specific system employing a ferricyanide/ferrocyanide redox couple. This couple is referenced as a non-limiting example, and is not intended as an indication that this couple is the only one that can be employed. Two electrodes 100 and 105 are placed in a substantially parallel configuration in electrolytic contact with a sample containing the species of interest. The geometry of the conduction cell does not limit the invention. The principles of operation are valid with many other geometries, including non-parallel facing configurations, different areas for each electrode, and coplanar configurations. In this example, the redox active compounds (RACs) are ferricyanide 125 and ferrocyanide 120, which form a redox couple. A potential source 110 imposes a potential difference between the two electrodes. In this example, Cathode Electrode 100 acts as the cathode, where a reduction reaction occurs to convert ferricyanide 125 to ferrocyanide 120; and Anode Electrode 105 acts as the anode where an oxidation reaction occurs to convert ferrocyanide 120 to ferricyanide 125. In this process, an electron 115 is transferred from the anode 105 to the cathode 100 for each molecule that reacts at a given electrode. Arrows 135 and 130 represent a transport process, such as diffusion, which contributes to the transport of species in the sample.

In some embodiments of the invention, the measured analyte species may be produced, consumed, and/or altered by other chemical reactions. FIG. 1 illustrates one example of this in an enzyme-linked biosensor where a substrate, such as glucose 500, reacts with an enzyme, such as glucose oxidase, to convert the enzyme from an oxidized state, GODox 510 to a reduced state, GODred 515. Ferricyanide 525, for example, can react with the reduced enzyme GODred 515 to convert it to its oxidized form GODox 510, in the process being reduced to ferrocyanide 520. Thus, the amount of ferricyanide and ferrocyanide, in this example, may be changed by other processes which may occur in the sample either before, during, or after measurement. The determination of ferrocyanide concentration, in this example, may then be related to the concentration of glucose.

Conduction cells such as the one illustrated in FIG. 3 can be used for determining the concentration in and transport properties of the analyte or RAC species through the sample medium (MacInnes, 1939). Such cells can be used by applying either a DC potential or an AC potential between the electrodes. AC potentials have been used to minimize the electrochemical reaction products at each electrode; however, depending on the needs of the application, either method could be used to determine transport properties of the analyte.

To determine the transport properties of a conductance cell, the current that flows through the cell in response to a voltage is measured. The resistance of the cell is computed by taking the ratio of the applied voltage to the resulting current. The conductivity, κ, of the sample may be computed by:

$$\kappa = \frac{h}{RA}$$

where h is the distance between the electrodes, R is the resistance, and A is area of each electrode, which are assumed to be equal. The cell constant of a conductance cell, $K_{cell}$, is defined by the quantity:

$$K_{cell} = \frac{h}{A}$$

Thus, if the cell constant for a conductance cell is known, then the conductivity of an unknown sample may be determined by measuring the resistance across the cell as follows:

$$\kappa = \frac{K_{cell}}{R}$$

Since the conductivity of the sample is a function of the concentration and transport properties of the analyte, the prior art has thus established a method of determining transport properties such as diffusion coefficient and mobility of an analyte due to concentration gradients and potential gradients, respectively, that can exist in a conductance-cell electrochemical sensor. How conductivity relates to factors such as transport properties and concentration depends on the specific nature of the experimental set up.

For this method to be successful, the cell constant must be known. The conventional method for doing this is to calibrate the cell using a sample of known conductivity to determine the cell constant and then use the same cell to measure the conductivity of an unknown sample (MacInnes, 1939).

Variations on this method are also known. Conductance measurements have been routinely used to determine both concentrations and transport properties in samples. For example, in water purification, the concentration of ionic species has been determined by conductance measurements. In another example, the diffusion properties of an analyte have been used to determine the level of particulate matter in a sample. In particular, one can use conductance measurements for determining the level of hematocrit in blood samples. One example of when this becomes particularly important is for electrochemical blood glucose sensors; the sensor reading may be significantly affected by the level of hematocrit or the viscosity of the blood sample since the transport properties, such as diffusion and/or migration, are affected.

For example, particulate matter such as hematocrit, and other factors, such as protein content, chylomicrons, and platelets, can affect the transport properties of many of the chemical species involved in performing blood-glucose measurements. Thus, much interest has been shown in quantifying the effects that transport properties have on the determination of analyte concentrations, such as glucose, that are computed by analytical instruments. Many factors can affect the transport, including but not limited to migration due to an electric field, diffusion due to a concentration gradient, and convection due to movement of the sample or temperature; and that an analogous approach may be used to correct for transport variations resulting from these factors. Convection effects can be minimized—and effectively removed—by having the electrodes in a conduction-cell system spaced less than 200 microns apart, and more preferably, less than 150 microns apart (Schmidt-Weinmar, 1967).

FIG. 3 illustrates one example embodiment of a cell that can be used for measurement. In this case, the target analyte is ferrocyanide 120, which in this example is taken to be a minority species. Ferricyanide 130 in this example is taken to be in excess, thereby being a majority species. Applying a sufficiently large electric potential between the electrodes 100 and 105 in contact with the sample will change the chemical potential of the nearby solution as the concentration of the minority species at one of them falls very close to zero while its concentration at the other electrode approximately doubles. In one example, if Electrode A 105 is at a sufficiently higher potential than Electrode C, then an oxidation process occurs at electrode A 105 and a reduction process occurs at Electrode C 100. One of ordinary skill in the art will recognize that the applied potential can also affect the distribution of ionic species and that this can be more fully expressed by the electrochemical potential, which includes the effects of this. The underlying pattern of behavior discussed here in terms of the chemical potential is therefore for illustrative purposes only and not to be taken as a convention. Other expressions of forces of equilibration on the species than those specifically disclosed herein are within the scope of the present invention. Examples of such forces include a thermodynamic force such as from a concentration gradient described in Atkins (1999) and force due to motion of the medium as in convection.

In an example of a method to extract the cell constant, $K_{cell}$, by applying a voltage to the cell and then removing electrical communication, drawn from an equivalent circuit model, the amount of charge stored in the conduction cell by creating concentration gradients can be expressed as:

Stored charge=$nF$*[ferrocyanide]*(Volume of cell)

A capacitance is therefore produced by charging to the applied voltage Vapp.

Capacitance=(stored charge)/$Vapp$

Capacitance=$nF$*[ferrocyanide]*(Volume of cell)/$Vapp$

Removing the electrical communication between the electrodes leaves the stored charge to discharge itself exclusively through the resistance R of the cell. In this equivalent circuit model, the time constant of this discharge can then be determined by standard methods from the variation of potential between electrodes over time, where:

Time constant=$R$*Capacitance

Since conductivity, $\kappa = K\text{cell}/R = \gamma$*[ferrocyanide] where $\gamma$ is a constant of proportionality, this implies $R = K\text{cell}/(\gamma$*[ferrocyanide])

hence, the time constant=$nF$*(Volume of cell)*$K\text{cell}/(\gamma$*$Vapp$)

which is a concentration independent measure of Kcell.

Another example embodiment from the perspective of ion mobilities considers a potential gradient along the distance between the two electrodes that will be created by applying a voltage to the cell. Movement of species along this gradient has been described in the prior art for current in a conduction cell (MacInnes, 1939). The movement of ferrocyanide in such as system has been described in terms of its mobility, U, in response to an electric field, $\vec{E}$. This equation appears as:

$$I_s = \beta \vec{E} U A \frac{C}{h}$$

$$K_{cell} = \frac{h}{A}$$

$$s = -U\vec{E}$$

$$I_s = -\beta C A \frac{s}{h}$$

where $I_S$ is the steady-state current, $\beta$ is a proportionality constant, s is the drift speed and $\vec{E}$ is the electric field. The ratio of h to A was typically calculated in a calibration step using a known standard to give the cell constant, $K_{cell}$. (Atkins, 1999). The drift speed is given as a negative number in this example since the current is taken to be carried by negative ions; thus, the drift speed of negatively charged ions will be in the opposite direction to the applied electric field. Other equations are possible for $I_S$, depending on the nature of the apparatus. In this example, there are a number of variables that can distort extracted concentration information from the electrochemical current. In practical measurements, the cell constant can vary from cell to cell since manufacturing variations can alter the geometric factors affecting the cell constant. Furthermore, when analyzing real samples, such as whole blood for glucose determination, the transport properties of the analytes—such as drift speed—may well vary between samples. For example, the level of hematocrit is known to affect the movement of chemical species in blood. Thus, signal variations due to factors other than the concentration, such as the variations of the cell constant and the drift speed, can significantly alter the estimated glucose concentration from an electrochemical sensor system.

The difficulty, therefore, is being able to quantify the error introduced by variations other than the analyte concentration, such as variations in the cell geometry and in the transport properties, to correct for estimates of analyte concentration. A method and apparatus for performing such an autocorrection would be useful. Embodiments of this invention describe a novel apparatus and method for determining and correcting for the environmental sources of measurement variation—that is, sources other than concentration—without a priori knowledge of the electrode area, the electrode separation, drift speed, or the mobility.

An analogous method and apparatus may be used for the motion of species due to a concentration gradient. In this example embodiment, a concentration gradient along the distance between the two electrodes will be created by the electrochemical reactions and movement of species along this gradient may be described by Fick's law of diffusion:

$$\text{Flux} = -D\frac{dc}{dx}$$

where D is a diffusion coefficient, dc/dx is the concentration gradient along a particular axis and Flux is the amount of substance that moves through a unit area perpendicular to this axis in a unit time. In one example where the flux reaches a steady state and where the electrodes are parallel, planar structures with the sample between them giving a wetted area, A, on each electrode and where the electrodes are separated by a distance, h, then the flux for an initial minority carrier concentration, C, will be:

$$\text{Flux} = -D\frac{2C}{h}$$

If n electrons are exchanged per molecule of minority carrier consumed electrochemically at one electrode or generated electrochemically at the other, then the steady-state current, $I_S$, generated by the movement of minority carrier may be given by:

$$I_s = nFDA\frac{2C}{h}$$

where F is Faraday's constant. Thus, the movement of an ion in terms of its mobility U under the force of an electric field $\vec{E}$ is equivalent to its movement in terms of its diffusion coefficient (with suitable adjustment of units) and so the term nFD can be expressed as $\beta \vec{E}$ U (Atkins, 1999). Thus, the invention may be applied to a system in terms of its diffusion as well.

According to an embodiment of the invention, the estimate of analyte concentration may be improved by determining and correcting for the errors introduced by unknown variations in apparatus factors, such as the cell geometry, and sample factors, such as the sample composition. A significant challenge in chemical sensors is to determine the concentration of the target analyte accurately since variations in the measurement environment—such as electrode separation or viscosity—can affect the estimate of analyte concentration. An apparatus and method that is sensitive to the effects of such variations but is substantially independent of analyte concentration could be used for estimating and correcting for these sources of variation.

According to an embodiment, the error in estimating analyte concentration that arises from different effective electrode areas can be reduced by using an apparatus and method that is sensitive to the effects of varying electrode areas but is independent of, or less dependent on, analyte concentration. This could be used for determining electrode area and thus allowing a correction to be applied to the concentration estimate that accounts for this variation.

According to an embodiment, the error in estimating analyte concentration that arises from different transport properties of analytes in samples can be reduced using an apparatus and method that is sensitive to these properties but is independent of, or less dependent on, analyte concentration. This could be used to determine the mobilities of analytes in samples and thus enable a correction to be applied to the estimate of analyte concentration that corrects for these.

Embodiments of the invention relate to determining certain parameters of the measurement system that can affect the measured signal and thus affect the estimated concentration. In one embodiment, the geometric cell parameters and the transport properties of the sample are taken as the representative sample factors and apparatus factors—other than analyte concentration itself—which can affect the measured signal. The effects of one component of the cell constant, h, and drift speed, s, may be combined into an Effective Transport Parameter ($P_T$) and may be considered separately from the electrode area term. In particular $P_T$ may be given by:

$$P_T = -\frac{h}{s}$$
$$C = -\frac{K_{cell} I_s}{\beta s} = -\frac{I_s h}{\beta s A} = \frac{I_s P_T}{\beta A}$$

One of ordinary skill in the art will recognize that an analogous expression may be given for a system under the influence of a concentration gradient which is better described in terms of a diffusion coefficient. In this case, $P_T$ can be given as follows:

$$P_T = \frac{h}{D}$$
$$C = \frac{\alpha K_{cell} I_s}{D} = \frac{I_s h}{2nFDA} = \frac{I_s P_T}{2nFA} = \frac{\alpha I_s P_T}{A}$$
$$\alpha = \frac{1}{2nF}$$

The effective electrode area, A, can be found by a method as described in our pending patent application number WO 03/069304. Thus, a method to determine $P_T$ allows for complete characterization of the measurement conditions and enable a more accurate estimate of the concentration. In a preferred embodiment, $P_T$ is determined substantially independent of electrode area and substantially independent of analyte concentration. However, this is not a requirement and does not limit the scope of the invention. An embodiment of the invention describes a method and apparatus that enable both the apparatus factors—such as the geometric properties of the cell—and sample factors—such as transport properties of the sample—to be found simultaneously, allowing for more complete autocorrection for variations in the measured signal that arise from environmental factors, sample factors, and apparatus factors. Prior art in the use of conduction cells has typically required that each conduction cell be calibrated in a separate step such and does not provide a means for auto-correcting for variations in the measured signal that arise from environmental factors, sample factors, and apparatus factors.

Figure 4:
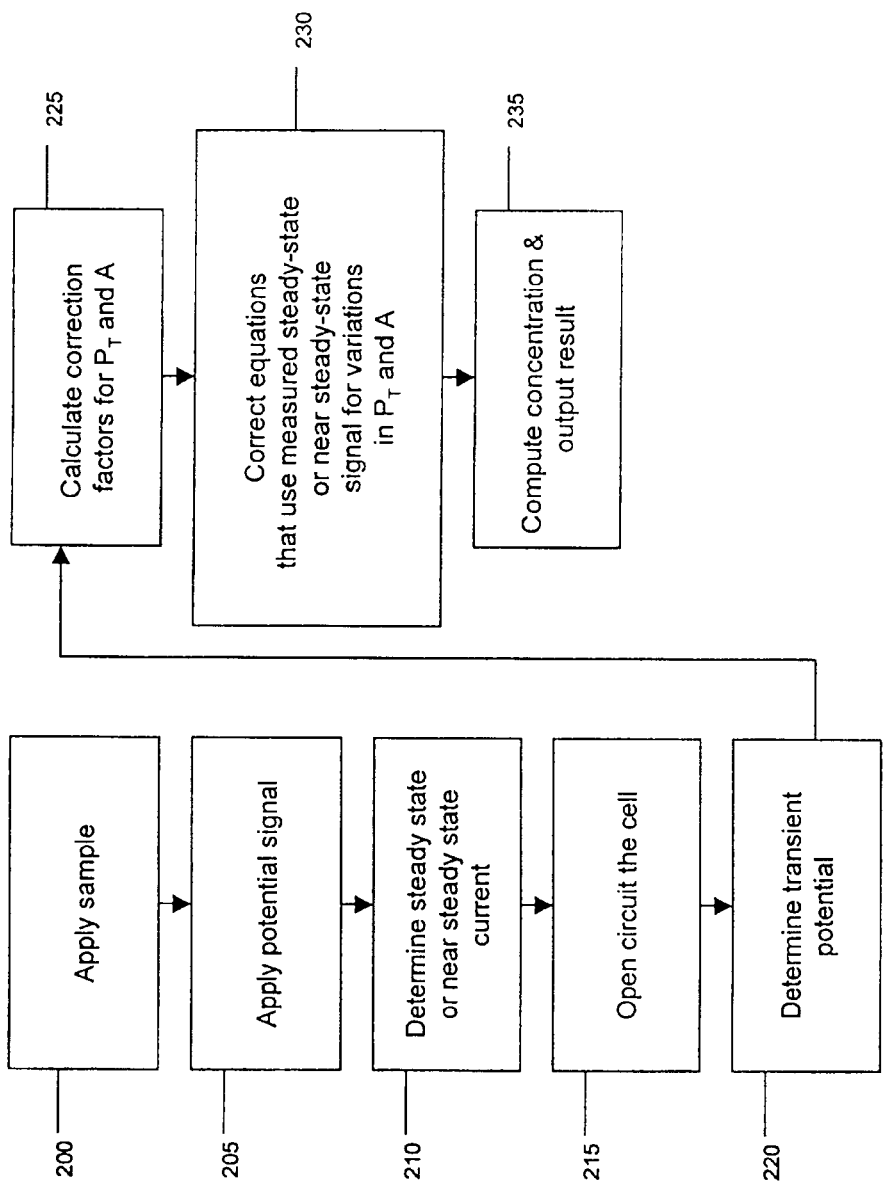
FIG. 4 illustrates one method for performing auto-correction in accordance with the invention.

FIG. 4 illustrates one method for performing auto-correction of such variations to increase the accuracy of the estimated analyte concentration. This diagram is an illustrative embodiment and does not limit the invention. One of ordinary skill in the art will recognize the possibility that these steps do not necessarily have to be executed in the stated order. A sample is applied to the cell (step 200), then a potential signal is applied to the cell (step 205). This potential signal should be such that a reduction and/or oxidation process occurs at at least one of the electrodes in the cell. One of ordinary skill will recognize that the potential signal need not necessarily be applied after the sample is applied to the cell but that the sample may be applied to the cell after the signal is applied. A steady-state current is determined from the cell (step 210). This current does not necessarily need to be a time-invariant current since time-varying currents may also be classified as steady-state if the characteristics that describe the signal are approaching a stable value.

Once this steady-state current has been determined, the cell is then open circuited (step 215) and the transient potential between the two electrodes is determined (step 220). One of ordinary skill in the art will recognize the possibility of other methods to maintain substantially zero electronic current between the electrodes other than by open-circuiting the cell. An example of another method includes the use of a high-impedance switch such as a transistor. The example embodiment of open-circuiting the cell (step 215) is an example and does not limit the invention. Correction factors for the environmental variations, for example those arising from variations in the drift speed, mobility, diffusion coefficient and/or from the cell constant, may be determined (step 225) based on information from the steady-state current before the cell has been open circuited and from the transient potential after the cell has been open circuited. The correction factors can then be used to correct the measured steady-state signal for variations caused by the environmental sources (step 230) and the corrected concentration estimate can be computed and output in a useful form (step 235). One of ordinary skill will recognize the possibility that the correction of the environmental sources of variations need not be a separate distinct step but may be integrated with the computation of the concentration. One of ordinary skill will also recognize that information of other parameters of the sample than analyte concentration may also be derived from the correction factors as separate, valuable information. Examples of such parameters include hematocrit, temperature, and viscosity.

In one embodiment, after $I_S$ is determined, the circuit is opened, and the transient potential between the electrodes is determined. One embodiment of realizing this is to have the measuring and control apparatus switch from a potentiostatic operating mode, where a potential is applied and a current is determined, to a galvanostatic operating mode, where a set current is maintained—in this case nearly 0 Amps—and a potential is determined. One of ordinary skill in the art will recognize that other embodiments—other than open-circuiting the cell—are possible for achieving substantially zero amps. One example is to use a high-impedance switch such as a transistor to restrict the current flowing in the circuit to substantially zero amps. The example of open-circuiting the cell is an example embodiment and does not limit the invention.

Once a steady-state current has been established, there will be a concentration gradient between the two electrodes. A factor that is related to $P_T$ can be determined by measuring the rate of relaxation of the electrode potentials upon removal of an imposed voltage between the electrodes. In the absence of an imposed voltage, the steady-state distribution of species— for example, such as a concentration gradient—will be unstable and the electroactive species will move in an attempt to restore a more stable concentration profile of molecules throughout the sample. The different relative concentrations of ferrocyanide ions and ferricyanide ions at each electrode will give different chemical potentials, and these chemical potentials will change with time as these concentrations equilibrate. This information can thus be monitored using potentiometric methods, and the measured change in potential with time can be related to $P_T$. Examples of methods to determine a measure of $P_T$ include:

1. The time from the point of removal of the imposed voltage for the potential to reach a particular value
2. The potential at a particular point in time after removal of the imposed voltage
3. A measure of the rate of decay of the potential after removal of the imposed voltage such as:
    The slope of the plot of the potential vs. time during a particular period of time
    The slope of the plot of the logarithm of the potential vs. time during a particular period of time
    The slope of the plot of $1/V^2$ vs. time during a particular period of time, where V is the potential Other quantities can be used to determine a measure of $P_T$ from monitoring the change in potential with time.

In the example of a conductance-cell sensor, the relaxation of the concentration profile upon removal of the imposed potential difference can be described by the following relationships (Atkins, 1999):

$$J = -D\frac{dc}{dx}$$
$$J = sc$$

If the conductance-cell sensor is switched from amperometric operation where a potential is applied to potentiostatic operation where the imposed potential is removed—and, in this example, a substantially zero current is maintained—and the potential is measured at time t=0, then at the initial relaxation stage (that is, at t=0+) the concentration gradient may be given as follows, and $P_T$ may be computed:

$$\frac{dc}{dx} = \frac{2c}{h}$$
$$sc = -D\frac{dc}{dx} = -D\frac{2c}{h}$$
$$s = -\frac{2D}{h}$$
$$P_T = \frac{-h}{s} = \frac{h^2}{2D}$$

In contrast to monitoring currents (see, e.g., U.S. patents: U.S. Pat. No. 5,942,102, U.S. Pat. No. 6,179,979, U.S. Pat. No. 6,284,125), monitoring the chemical potentials at the electrode will therefore allow for a measurement that is independent of the area of the electrode. When the steady-state concentration gradient relaxes under potentiometric conditions (i.e. no electrochemical transfer of charge from one electrode to another via an electronic current) the concentration profile changes, and a computer-simulated model of this is shown in FIG. 5.

Figure 5:
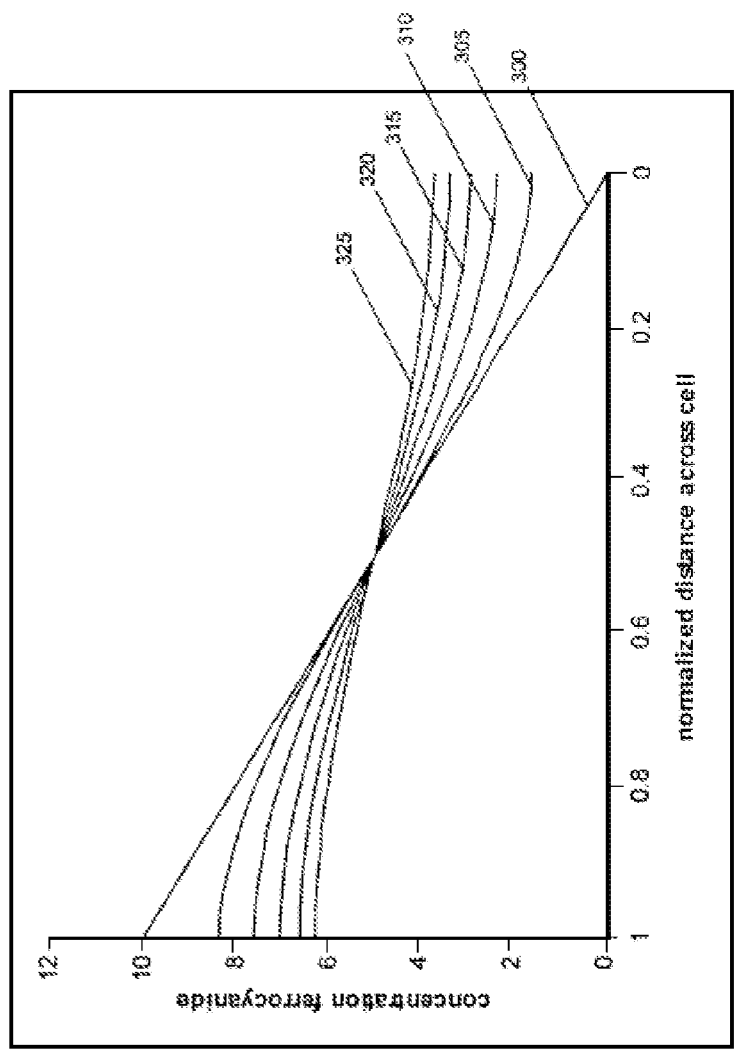
FIG. 5 shows results of a computer simulation of the relationship between ferricyanide concentration and normalized distance across an electrochemical cell at different times after open-circuiting the cell.

The simulation results shown in FIG. 5 model the cell illustrated in FIG. 5 where Anode Electrode 105 is located at x=0 in FIG. 5 and Cathode Electrode 100 is located at x=1 in FIG. 5. The distance between the electrodes has been normalized to 1 unit. The concentration profile of ferrocyanide can be seen to evolve with time. A steady-state concentration profile exists when a steady-state current is realized and before the circuit is opened, given by 300. The circuit is opened at t=0 seconds and the concentration profile is shown at the following times: t=0.2 sec 305, t=0.4 sec 310, t=0.6 sec 315, t=0.8 sec 320, and t=1.0 sec 325. The chemical potential difference between species at what was the anode (Anode Electrode 105) and cathode (Cathode Electrode 100) can be described by:

$$V = \mu_{anode} - \mu_{cathode} = \frac{nF}{RT}\left(\ln\left(\frac{a(\text{ferrocyanide})_{anode}}{a(\text{ferricyanide})_{anode}}\right) - \ln\left(\frac{a(\text{ferrocyanide})_{cathode}}{a(\text{ferricyanide})_{cathode}}\right)\right)$$

where µ is the chemical potential of the ferrocyanide/ferricyanide couple, a(species) is the activity of that species, and subscripts refer to the position in the cell. The activity of the species is related to the concentration, but is a more ideal form that accounts for deviations in thermodynamic quantities from those predicted purely by concentration; however, using concentrations, the potential difference at the electrodes can be approximated by:

$$V = \frac{nF}{RT}\ln\frac{[\text{ferrocyanide}]_{anode}}{[\text{ferrocyanide}]_{cathode}}$$

where [ferrocyanide]$_{electrode}$ is the concentration of ferrocyanide at the appropriate electrode, and [ferricyanide] is assumed to be in large excess throughout the sample and so may be approximated as remaining substantially constant throughout the sample and at the various times of interest. The evolution of this voltage over time has been modeled and is presented in FIG. 6 for various values of $P_T$. In this figure, the potential is determined as it is relaxing after the circuit has been opened at time t=0 for the following values of $P_T$: $P_T$=28.7 s 420; $P_T$=19.2 s 415; $P_T$=11.6 s 410; $P_T$=5.9 s 405; $P_T$=3.8 s 400. There is a clear effect of $P_T$ on the time constant of the relaxation; it will be clear to one ordinarily skilled in the art that other relationships may exist depending on apparatus factors, sample factors, and/or environmental factors, such as the cell configuration and measurement method.

Potentiometry measurements can therefore be used to determine $P_T$ from the variation between measured potential and time; the evolution of the potential relaxation is substantially independent of the analyte concentration and electrode area but is a function of $P_T$, thereby providing a needed method for determining a correction factor for variation in $P_T$. It will be clear to one of ordinary skill in the art that there are a variety of methods of using this potential variation to quantify the effect of $P_T$. Examples of such methods include determining a slope of the potential relaxation during an interval of time, determining the time it takes to reach a particular potential value, and/or determining a time constant for the decay rate for the potential relaxation.

Figure 6:
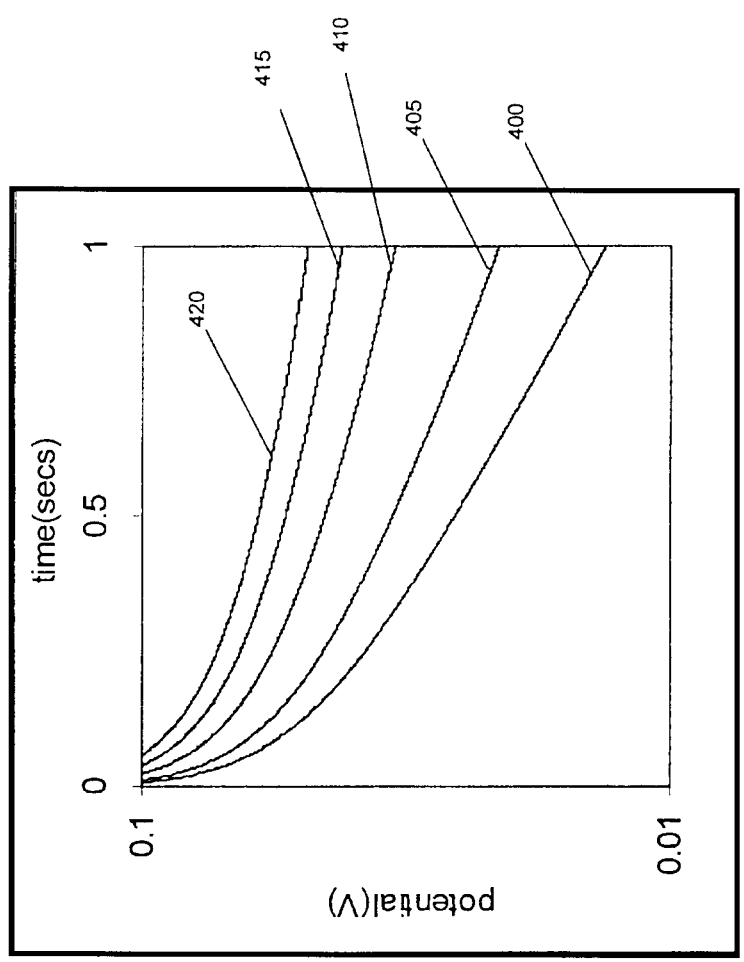
FIG. 6 shows the decay of potential as a function of time for various values of $P_T$.

FIG. 6 illustrates one example embodiment of determining a measure of $P_T$. In this example, the time taken to reach a potential difference of 0.06 V after switching to potentiometric operation is measured for different values of $P_T$. It is clear that the time taken to reach a given potential difference upon potentiometric relaxation of the conduction cell can be a measure of $P_T$ and therefore, the embodiments of the invention provide a means for determining a measure of $P_T$. When a value for the effective electrode area is determined, then variations in sample factors, apparatus factors, and environmental factors (including factors such as the effects of cell geometry and transport of analyte) which can contribute to variations in effective electrode area and/or variations in $P_T$ can be corrected to determine a more accurate estimate of analyte concentration. For example, one method of determining an effective electrode area has been disclosed in PCT 03/069304 and is also described above. This method involves the application of a small amplitude sine wave to the electrodes and relating the resulting sinusoidal current to the electrode area via a set of appropriately constructed equations. When a sample is measured by such a conductance-cell electrochemical sensor, $I_S$ can be directly measured and determined, $P_T$ can be determined by the method and apparatus of embodiments of the invention, A can be determined by the previously described methods, and other constants can be computed a priori, thereby giving a more accurate estimate of the concentration.

Figure 7:
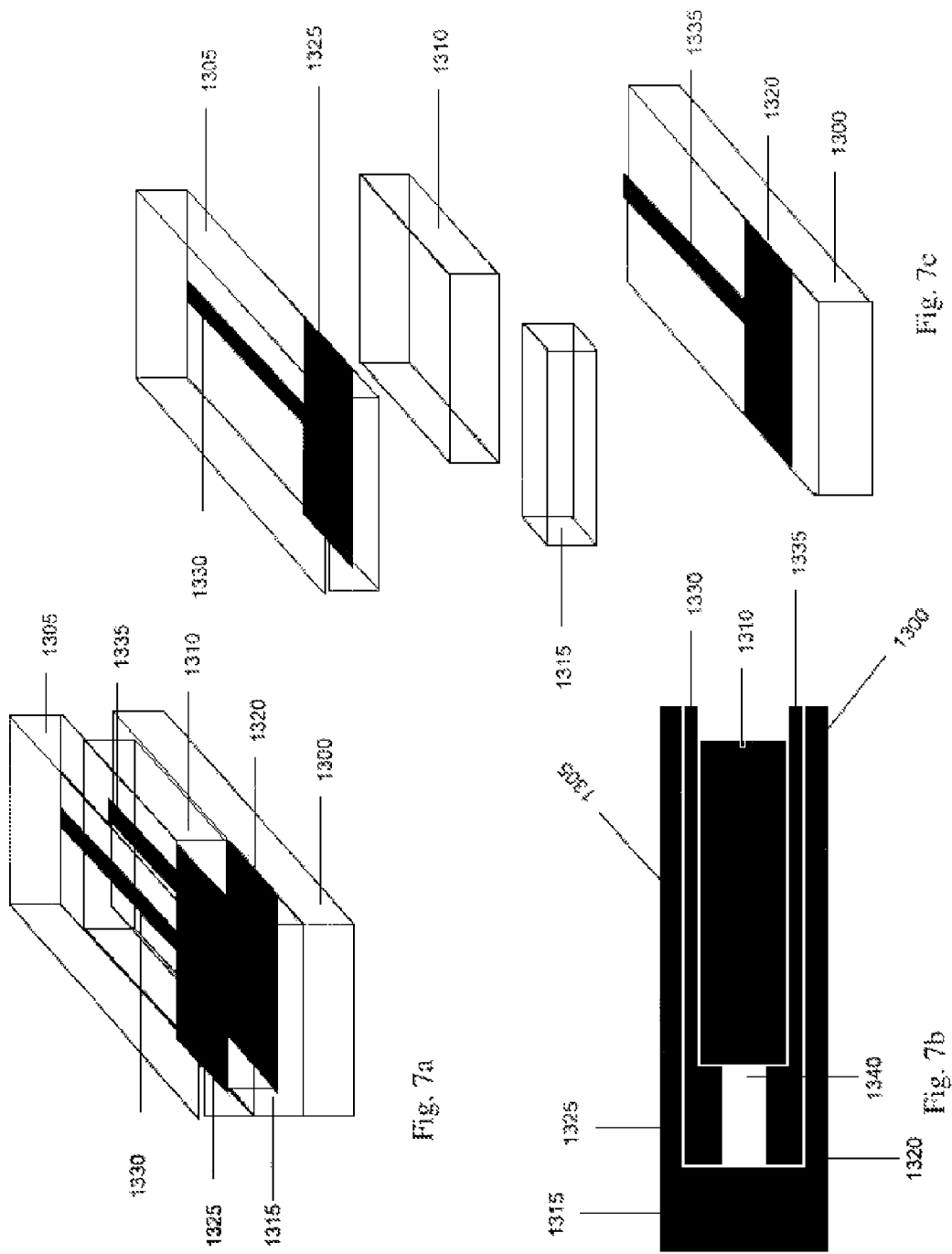
FIGS. 7A-C illustrate an embodiment of the electrochemical cell of a conduction-cell electrochemical sensor.

FIGS. 7A-C illustrate an embodiment of the electrochemical cell of a conduction-cell electrochemical sensor. FIG. 7A shows a composite three-dimensional schematic drawing for such an apparatus; FIG. 7B shows a schematic drawing of a side view; and FIG. 7C shows a schematic drawing of some of the components that comprise the apparatus separated from a composite construction. This example embodiment is comprised of a conduction cell with substantially parallel electrodes (1320 and 1325) separated by a volume 1340 which can hold a sample and substantially defines a sample chamber. This volume 1340 is herein referred to as "sample chamber". Each of the electrodes (1320 and 1325) is supported by a substantially nonconductive material (1300 and 1305). Each of the electrodes (1320 and 1325) has electrical connections provided by substantially conductive paths (1335 and 1330) that are also supported by a substantially nonconductive material (1300 and 1305). The thickness of the electrodes (1320 and 1325) may be substantially the same as, substantially less than, or substantially greater than the thickness of the leads (1330 and 1335). The two electrodes are kept separated by substantially nonconductive material (1325 and 1310). The volume where the sample is placed (1340) may be partially defined by the electrodes (1320 and 1325) and/or partially defined by the substantially nonconductive material (1320 and 1315).

Figure 8:
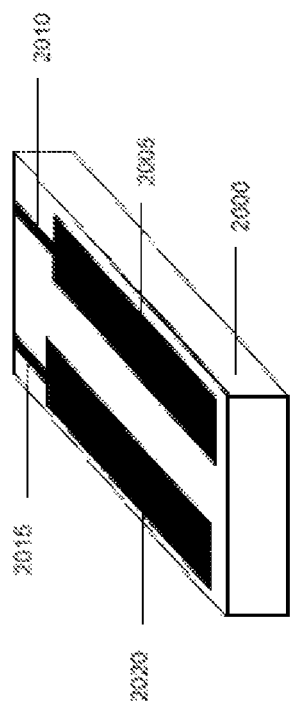
FIG. 8 shows a cell with side by side electrodes.

In an exemplary embodiment, two facing, and substantially parallel, sides of the sample chamber 1340 are substantially defined by the area spanned by two electrodes (1320 and 1325), as illustrated in the schematic of FIGS. 7A-C. The apparatus of FIGS. 7A-C illustrates one example embodiment of the electrochemical cell 50 illustrated in FIG. 2. One of ordinary skill in the art will recognize that other embodiments are possible. For example, the electrodes need not be substantially parallel to each other. In another example, the electrodes may lie in the same plane, and illustrated in FIG. 8. In this example embodiment, electrodes 2005 and 2020 lie in the same plane on a substantially nonconductive substrate 2000. Electronics connectors 2010 and 2015 provide a means of electronic coupling between the electrodes (2005 and 2020) and the TCA. Thus, there are many different geometric configurations that can be used for a conductance-cell sensor. The example discussed in this document is one example embodiment and does not limit the invention.

In the apparatus of FIGS. 7A-C, the two electrodes (1320 and 1325) can be operated as either Electrode A 55 or Electrode B 60. The sample 70 is substantially located in the sample chamber 1340. Electrical contact with the Transducer Control Apparatus 5 is achieved via the substantially conductive paths (1335 and 1330) which can be electronically coupled to the Transducer Control Apparatus 5 to provide a substantially conductive electronic path from the Transducer Control Apparatus 5 to the electrodes (1320 and 1325). One example embodiment of electronically coupling the Electrochemical Cell of FIG. 13 to the Transducer Control Apparatus 5 is to provide a means of substantially contacting a region of each of the substantially conductive leads (1330 and 1335) to a portion of the TCA 5. One exemplary example of such a means is to substantially contact that region of each of the substantially conductive leads that are furthest away from the region in contact with the electrodes (1320 and 1325). In the example schematic illustration on FIG. 7A-C this is illustrated by that portion of the substantially conductive leads (1330 and 1335) that extends beyond the substantially nonconductive material 1310. One of ordinary skill in the art will recognize the possibility of other means of electronically coupling the Electrochemical Cell 50 illustrated in FIGS. 7A-C to the transducer Control Apparatus 5.

In one exemplary example embodiment, the apparatus of FIGS. 7A-C can be used according to the process illustrated in FIG. 3. In one embodiment, one of the electrodes 1320 in the cell is the Cathode Electrode 100 and the other electrode 1325 is the Anode Electrode 105. In another embodiment, one of the electrodes 1325 in the cell is the Cathode Electrode 100 and the other electrode 1320 is the Anode Electrode 105. The ferricyanide 125 and the ferrocyanide 120 are substantially located in the sample chamber 1340. The voltage source 110 is provided by the Transducer Control Apparatus 5 and the current 115 travels along a substantially conductive path that is in part comprised of the substantially conductive leads (1330 and 1335). The transport processes (130 and 135) substantially occur inside the sample chamber 1340.

Apparatus of the Invention

A further aspect of the present invention provides an apparatus for use in practicing the method of the invention. Thus, the invention provides an apparatus for determining the presence of an analyte in a sample disposed in an electrochemical cell said electrochemical cell comprising two electrodes between which the sample is placed for analysis, said apparatus comprising:

(a) a housing having a space for receiving the electrochemical cell;

(b) means for applying a potential or a current between the two electrodes of the electrochemical cell when it is received within the housing (for example a potentiostat or a galvanostat);

(c) means for measuring oxidation or reduction of an analyte or a mediator in an analyte-detection system occurring within the electrochemical cell when the potential or current is being applied (e.g. a circuit for measuring/observing a current or a potential difference between the electrodes);

(d) means for switching the potential or current off after a period of time during which a chemical potential gradient is established between the two electrodes (e.g. a switch that open circuits the cell, or a high-impedance switch);

(e) means for monitoring the decay of the chemical potential gradient after the potential or current is switched off (e.g. a circuit for observing the potential difference between the electrodes);

(f) programmed data processing means for combining the measured oxidation or reduction with the monitored decay to produce an indication of the presence of the analyte in the sample (e.g. a data processor with accompanying programming that performs the steps described in this application); and (g) output means for conveying the indication of the presence of the analyte in the sample to a user.

The apparatus may be supplied separately, but is generally used in combination with an electrochemical cell in the form of a single use test strip. The apparatus has a slot for receiving the test strip, and appropriate signal generating and processing elements for applying the potential and current and for monitoring the result current or potential and the decay of the chemical potential gradient, and for converting the resulting information into an indication of the results of the evaluation. The test strip may be any test strip appropriate for the detection of the particular selected analyte. In preferred embodiments, the strip has facing electrodes and a spacing between the electrodes that is sufficiently short that the gradient of oxidized and reduced species extends across at least 10%, more preferably more than 80%, up to 100% of the distance between the electrodes. In general, this will be a distance of 20 to 400 microns. A display may be incorporated as part of the meter, for example in the form of an LCD display, an LED display, or moving coil meter. The display may also be separate from the meter, and connected with a wired or wireless communications link to the meter.

Figure 22:
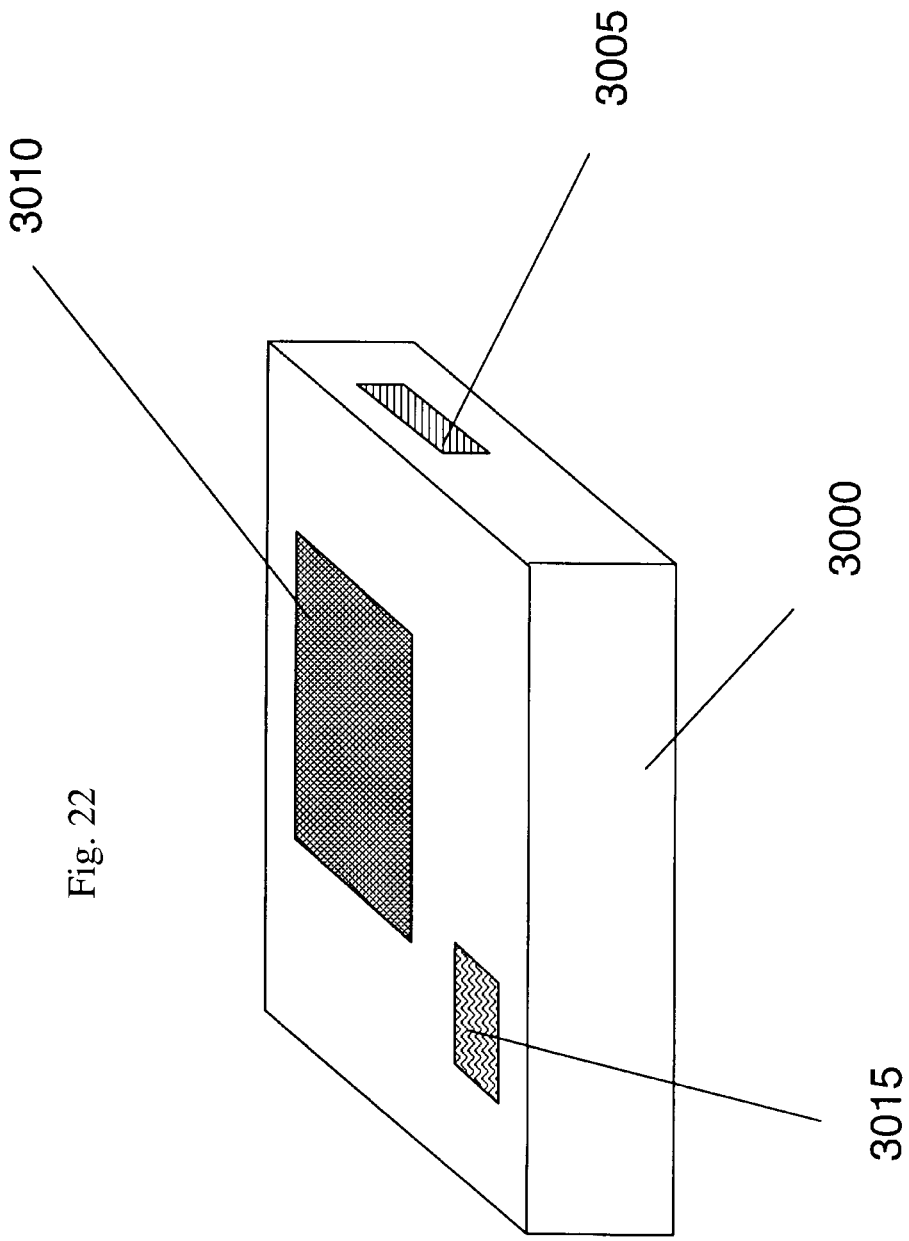
FIG. 22 shows an external view of an embodiment of an apparatus in accordance with the invention.

FIG. 22 shows an external view of an embodiment of the apparatus of the invention. Housing 3000 can be made from any suitable material, but will most commonly be made of an impact resistant plastic. Housing 3000 has an opening 3005 for receiving a test strip that comprises electrodes and connectors for making electrical contact between the test strip and the apparatus. A display 3010 provides output in a form readable by the user. Optionally, the apparatus can include a start button 3015, although detection of an inserted test strip may also be used to start the apparatus for processing of an analyte test.

Determination of Effective Electrode Separation

Independent of or in conjunction with the determination of analyte concentration, the methods of the invention can be used to determine the effective electrode separation between two electrodes in an electrochemical cell. Thus, in a further aspect, the present application provides a method for determining the effective separation distance between a first electrode and a second electrode in an electrochemical cell, the method comprising the steps of:

applying an external force in the form of an applied potential or an applied current to generate a chemical potential gradient between the first electrode and the second electrode;

stopping the application of the external force;

observing the decay of the chemical potential gradient as a function of time; and computing the effective electrode separation distance from the observed decay of the chemical potential gradient.

Determination of an Effective Transport Property

Independent of or in conjunction with the determination of analyte concentration, the methods of the invention can be used to determine an effective transport property of an electrochemical system. Effective transport properties include mobility of species, diffusion characteristics of species, and combinations of these properties with the effective electrode separation.

The following examples illustrate example embodiments of the method and apparatus of the invention.

Example 1

Correcting for Variations in $P_T$

Figure 9:
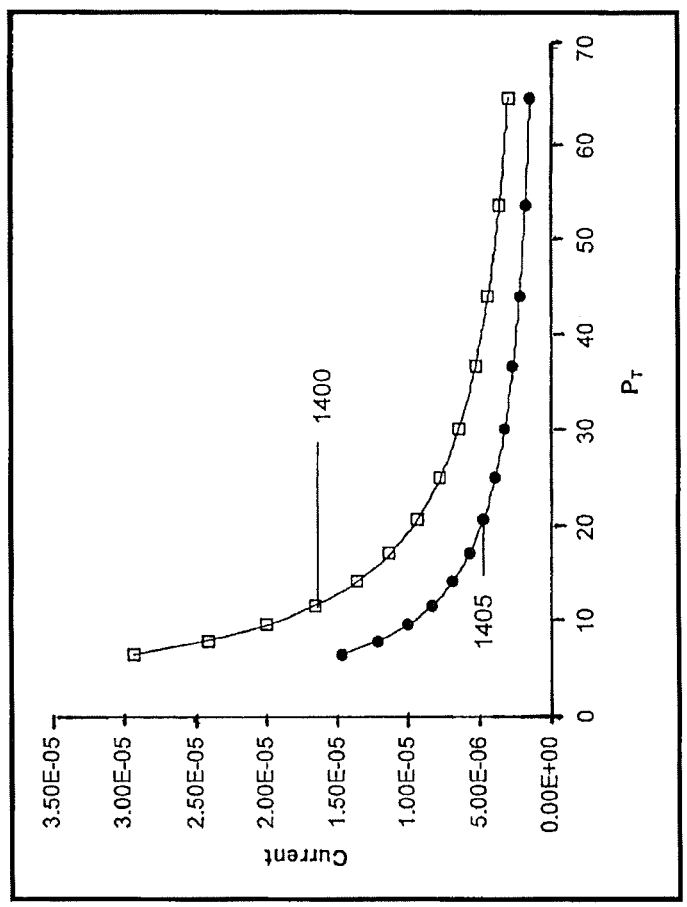
FIG. 9 shows one example relationship than can exist between $P_T$ and the measured current for different analyte concentrations.

One example of using $P_T$ to increase the accuracy of electrochemical sensor measurements is discussed. FIG. 9 shows one example relationship than can exist between $P_T$ and the measured current for different analyte concentrations. The data in FIG. 9 was simulated according to a conduction-cell electrochemical sensor as illustrated by the example drawings in FIG. 3 and FIGS. 7A-C. FIG. 9 illustrates the variation in current (given in amps) for different values of $P_T$ for a sensor comprised of each electrode having an effective surface area of 1 cm². Data points are shown in FIG. 9 for the steady-state current that is generated by the application of a voltage difference of 0.4 V between the two electrodes for a sample comprised of 2 mM ferrocyanide 1400 and 1 mM ferrocyanide 1405. It is clear that the measured current is dependent upon both the concentration of analyte and the value of $P_T$. Thus, variations in the value of $P_T$ can cause signal variations that can introduce error into the measurement of analyte concentration.

Figure 10:
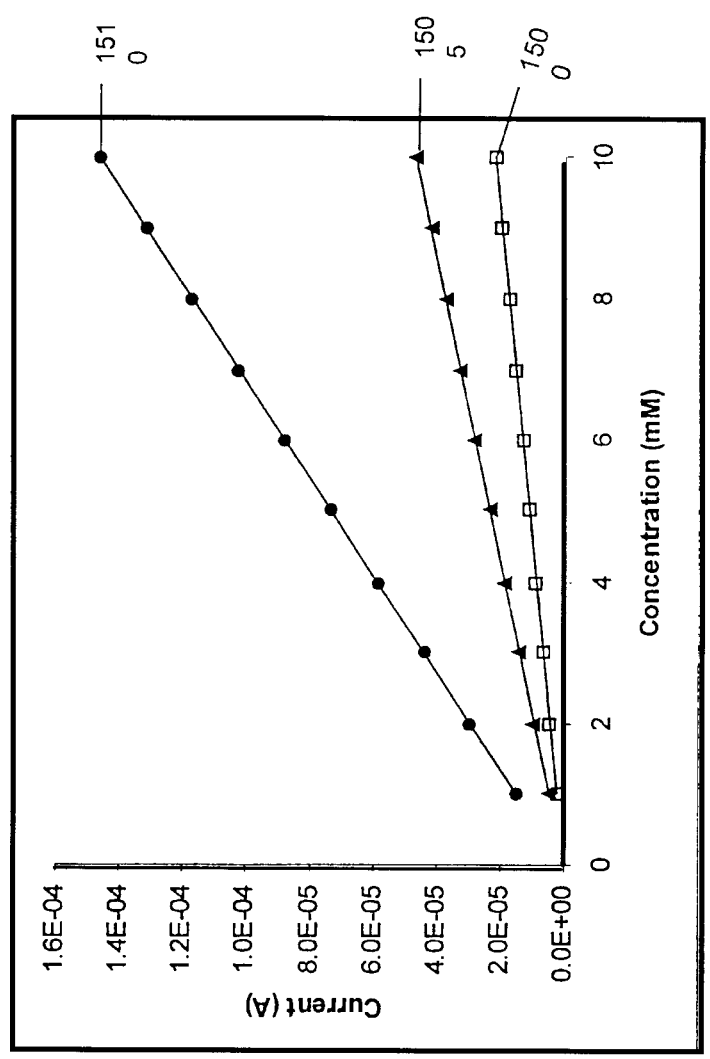
FIG. 10 shows representative calibration curves for different values of $P_T$.

FIG. 10 illustrates this problem further by showing representative calibration curves for different values of $P_T$. In this figure, the concentration is given on the x-axis in mM, and the measured steady-state current is given on the y-axis in amps. Data points 1500 correspond to a $P_T$ value of 44.3 s; data points 1505 correspond to a $P_T$ value of 20.6 s; data points 1510 correspond to a $P_T$ value of 6.58 s. Again, the error in analyte estimation that can arise from variations in $P_T$ is illustrated. If one particular calibration curve is taken to be the reference calibration curve, then this implicitly assumes that a particular value of $P_T$ is associated with the measurement. However, if the value of $P_T$ varies when an unknown sample is measured, then the resulting estimate in analyte concentration may be erroneous.

Figure 11:
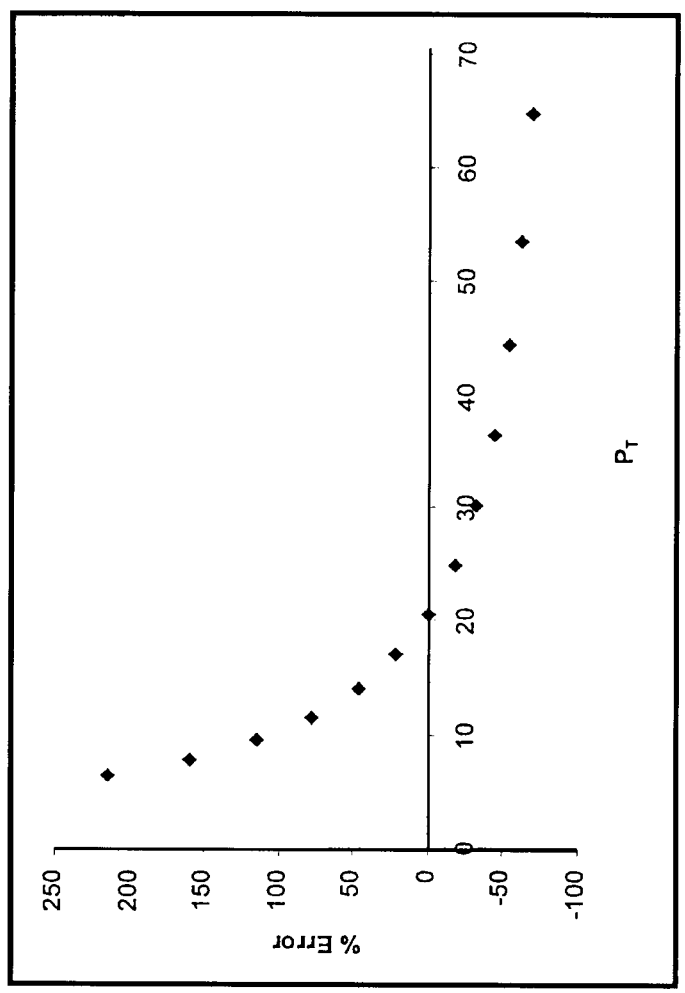
FIG. 11 illustrates one example of the type of error that may arise if the value of $P_T$ varies.

FIG. 11 illustrates one example of the type of error that may arise if the value of $P_T$ varies. In this example, the calibration curve is comprised of data points 1505 from FIG. 10; this calibration curve was determined for a system with a value of $P_T$ equal to 20.6 s. An equation to describe this calibration curve is:

$$I = (4.673E-6)[\text{ferrocyanide}]$$
$$[\text{ferrocyanide}] = \frac{I}{(4.673E-6)}$$

where I is the measured current, and [ferrocyanide] is the concentration of ferrocyanide in the sample. Thus, a measurement of the current can be used to estimate the concentration of analyte—in this example, ferrocyanide—in a sample by using the above equation.

FIG. 11 illustrates the error which may occur in estimating the analyte concentration if the value of $P_{T\ for\ the\ meaurement}$ were to be different from the value of $P_T$ that was used when determining the calibration curve. Current measurements are determined from a system with a 2 mM ferrocyanide concentration for different values of $P_T$. As the value of $P_T$ varied, the measured current varied. Since the estimation equation is determined from a calibration curve that was determined from a system that has a particular value of $P_T$, if measurements are made with a system that has a different value of $P_T$, the resulting estimation equation will yield an inaccurate estimate. FIG. 11 illustrates the error in analyte estimation that can occur for different values in $P_T$. The y-axis of the chart in FIG. 11 is the percent error in the estimate of ferrocyanide concentration as determined by the following:

$$\% \text{ Error} = 100 \times \frac{[\text{ferrocyanide}]_{estimate}}{[\text{ferrocyanide}]_{actual}}$$

$$[\text{ferrocyanide}]_{estimate} = \frac{I_{measured}}{(4.673E-6)}$$

$$[\text{ferrocyanide}]_{actual} = 2mM$$

Figure 16:
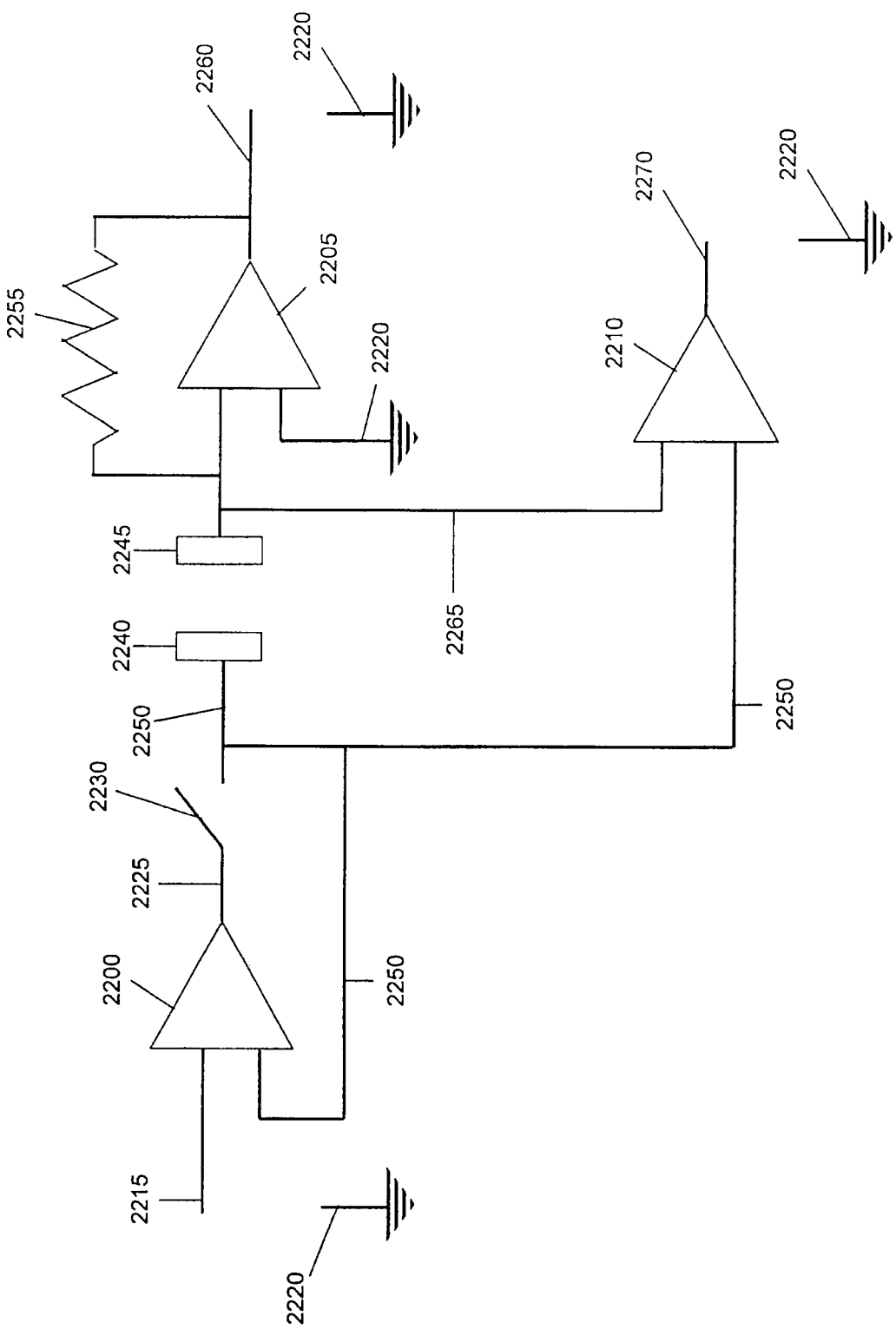
FIG. 16 shows an embodiment of a transducer control apparatus.

$I_{measured}$ is the measured current; [ferrocyanide]$_{actual}$ is the actual ferrocyanide concentration in the sample (2 mM, as indicated above); [ferrocyanide]$_{estimate}$ is the estimated ferrocyanide concentration as determined by an equation describing the calibration data 1505. FIG. 16 illustrates an example of the error in estimating analyte concentration that can occur if the value of $P_T$ changes from the value that was used when determining the calibration data. The data points represent the percent error in estimating the analyte concentration for different values of $P_T$. For reference, it should be noted that a value of $P_T$ equal to 20.6 s was used when determining the calibration data 1505. Thus, there is substantially zero percent error in the data of FIG. 11 when $P_T$ equals 20.6 s.

It is also noteworthy to observe that as $P_T$ increases, the rate of change in the error decreases. Likewise, as $P_T$ decreases, the rate of change of the error increases. One example of a situation that can give rise to small values of $P_T$ is when the distance between the two electrodes in a conduction cell sensor decreases. For example, the distance between the electrodes 1320 and 1325 in FIGS. 7A-C may be reduced by decreasing the thickness of the substantially nonconductive material 1310 and 1315. By decreasing this distance, the volume of the sample chamber 1340 also decreases. Thus, the influence of $P_T$ on an analyte estimate increases as the volume of the sample chamber decreases, further highlighting the usefulness and importance of being able to correct accurately for variations in $P_T$ at small sample volumes.

One example of using $P_T$ to correct an analyte estimate for errors caused by variations to $P_T$ includes determining a relationship between $P_T$ and the time t needed for potentiometric relaxation to reach a particular potential difference. In this example, a DC potential difference of 400 mV was applied to the electrodes for the simulated system of FIG. 3. Once a steady-state current was established, the potential difference was removed by open-circuiting the system—thereby ensuring that substantially no electronic current flowed in the circuitry—and the potential between the electrodes was monitored over time.

The simulation was executed for different values of $P_T$, and the relaxation of the potential difference over time was determined for each of these different values of $P_T$. The evolution of this potential over time has been modeled and is presented in FIG. 5 for various values of $P_T$. In this figure, the potential is determined as it is relaxing after the circuit has been opened at time t=0 for the following values of $P_T$=28.7 s 420; $P_T$=19.2 s 415; $P_T$=11.6 s 410; $P_T$=5.9 s 405; $P_T$=3.8 s 400.

The rate of relaxation of the potential between the two electrodes is substantially independent of analyte concentration. Thus, the usefulness of this technique is that it can be used to monitor properties of the system that give rise to the value of $P_T$ while not being substantially influenced by the analyte concentration. This is in stark contrast to prior-art methods which rely on monitoring relaxation currents, which are substantially influenced by analyte concentration (U.S. patents: U.S. Pat. No. 5,942,102, U.S. Pat. No. 6,179,979, U.S. Pat. No. 6,284,125).

Furthermore, monitoring the potential difference between the electrodes is a measure that is substantially independent of the area of the electrodes. This has the useful benefit of removing yet another potential source of variation from the measurement. This contrasts with methods that rely on monitoring relaxation currents, since the measured current value is dependent on the effective electrode area.

Figure 12:
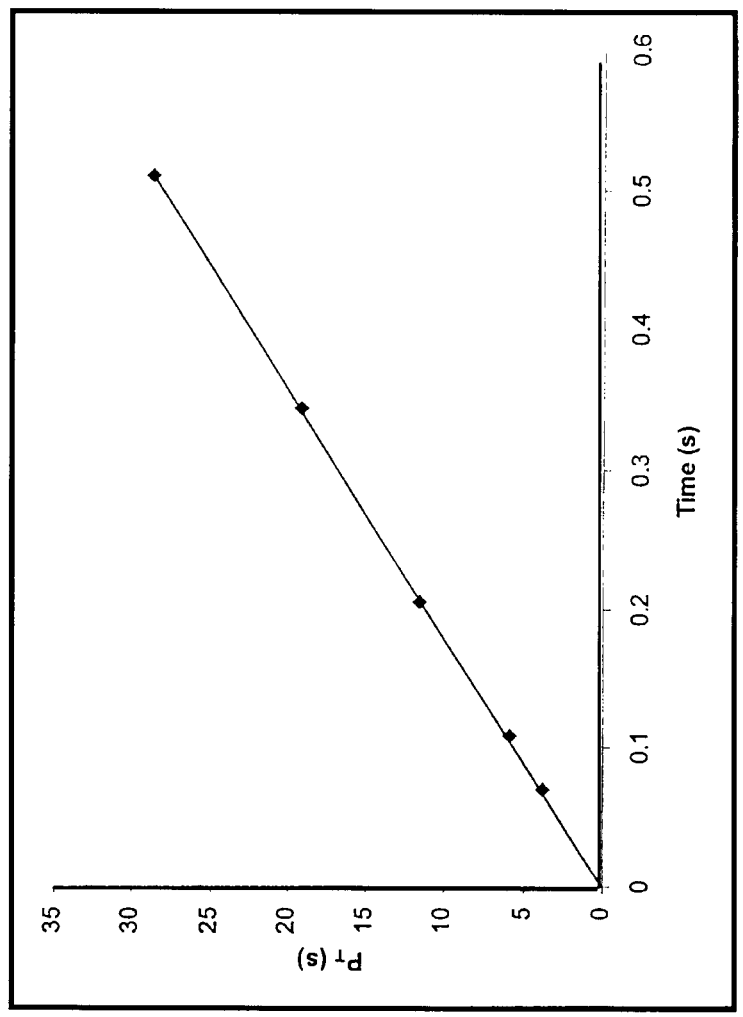
FIG. 12 illustrates a relationship between $P_T$ and the time t taken to reach a potential difference of 0.06 V.

One example embodiment for extracting a measure of $P_T$ is to determine the time taken from the start of potentiometric relaxation until a particular value of the potential is reached. This represents one metric for quantifying a measure of the rate of relaxation—or the time constant for the rate of decay—of the potential upon open circuiting the electrochemical system. One of ordinary skill in the art will recognize that other metrics can be used, such as the potential at a particular point in time, the slope of the potential vs. time plot during a particular period of time, the slope of the plot of the logarithm of potential vs. time during a particular period of time, and the slope of the plot of $1/V^2$ vs. time during a particular period of time, where V is the potential. FIG. 12 illustrates a relationship between $P_T$ and the time t taken to reach a potential difference of 0.06 V, where t=0 is the time at which the system is open-circuited. In this example, data shown in FIG. 6 was analyzed by determining the time at which the relaxing potential reached a value substantially equal to 0.06 V. Thus, each value of $P_T$ results in a different decaying potential and corresponds to a different time at which the potential reached a value that is substantially equal to 0.06V. FIG. 12, therefore, illustrates the relationship that exists between $P_T$ and a measure of $P_T$—in this example, the time taken to reach 0.06V and so allows a mathematical relationship to be established to determine $P_T$ from a measurable quantity of the potentiometric relaxation data. In this example, the following relationship is observed between $P_T$ and the time to reach the designated potential:

$$P_T = mt$$

$$m = 56.057$$

Other relationships may exist and such relationships may depend on the measurement set up, including the geometry of the electrochemical cell.

Since this potentiometric relaxation measurement is substantially independent of the analyte concentration, it can be used to estimate a measure of $P_T$ that is substantially unaffected by analyte concentration. This measure of $P_T$ may then be used to adjust for errors in the estimate of analyte that may arise from variations in the value of $P_T$. In this example, a calibration curve was determined for a system with $P_T$=20.6 s. As discussed earlier, one equation to estimate the concentration of an analyte may be given by:

$$P_T = -\frac{h}{s}$$

$$C = -\frac{K_{cell} I_S}{\beta_S} = -\frac{I_S h}{\beta_S A} = \frac{I_S P_T}{\beta A}$$

in terms of the mobility of the analyte species. One of ordinary skill in the art will recognize that other forms are possible, depending on the nature of the system. In one example discussed earlier, the concentration of an analyte may be given in terms of its diffusion properties by the following:

$$P_T = \frac{h}{D}$$

$$C = \frac{\alpha K_{cell} I_S}{D} = \frac{I_S h}{2nFDA} = \frac{I_S P_T}{2nFA} = \frac{\alpha I_S P_T}{A}$$

$$\alpha = \frac{1}{2nF}$$

In practice, a calibration curve is determined empirically since it is often more convenient to determine a proportionality constant by experimentation than determining all of the relevant components independently. For example, taking the system described in terms of analyte mobility as discussed above, one equation to describe the calibration data 1505 in FIG. 10 is:

$$I = \frac{1}{\lambda}[\text{ferrocyanide}]$$

$$[\text{ferrocyanide}] = \lambda I$$

$$\lambda = 2.14E5 mM/A$$

$$[\text{ferrocyanide}] = \lambda I = \frac{IP_T}{\beta A_e}$$

$$\lambda = \frac{P_T}{\beta A_e}$$

$$A = 1 \text{ cm}^2$$

$$P_T = 20.6s$$

$$\Rightarrow \beta = 9.63E-5$$

$$\Rightarrow \lambda = \frac{P_T}{9.63E-5} = (1.03E4)P_T$$

The proportionality constant λ incorporates the effects of the relevant parameters on the concentration estimate. Since this data 1505 was acquired on a system with a value of $P_T$ equal to 20.6 s, the constant λ may be expressed to explicitly incorporate the value of $P_T$, as indicated above. This then allows for a useful adjustment to be made for variations in $P_T$ that may introduce errors into the analyte estimate.

One example of correcting for errors in analyte concentration estimates that may arise from variations in $P_T$ is to adjust the description of the calibration curve to account for variations in $P_T$. More generally, the proportionality constant of a calibration curve λ may be given relative to the value of $P_T$ that was associated with the calibration data, indicated by $P_{T\ calibration}$. In this example, the value of λ can then be adjusted by the quantity $$\left(\frac{P_{Tcalibration}}{P_{Tmeasured}}\right)$$

such that:

$$\lambda = 2.14 \times 10^5 \left(\frac{P_{Tcalibration}}{P_{Tmeasured}}\right)$$

where $P_{Tmeasured}$ is the value of $P_T$ associated with the measured current signal $I_{measured}$. This then allows for adjusting a parameter λ—that, in part, defines a calibration curve—in response to variations in $P_T$ when measuring a sample. Thus, by obtaining a measure of $P_T$ that is substantially independent of $I_{measured}$ and the analyte concentration, the calibration curve that is used for estimating the analyte concentration may be adjusted to reduce an error in estimate of the analyte concentration. Embodiments of the invention provide a method for determining $P_T$ that is substantially independent of analyte concentration and measured current. One embodiment of the method to adjust for a variation in $P_T$ is to use embodiments of this invention to determine a measure of $P_T$ and adjust a parameter that in part defines a calibration curve. One example embodiment of this method is to multiply the calibration factor λ by the correction factor $$\left(\frac{P_{Tcalibration}}{P_{Tmeasured}}\right)$$

and then use this adjusted value of λ in estimating the analyte concentration. The following equations illustrate this example embodiment. From calibration data 1505 in FIG. 10, an equation is determined that substantially models this data. One example embodiment in determining such an equation is to use well-known linear regression techniques to find a linear equation that best describes this data 1505. One example of such an equation is given by the following:

$$C_{calibration} = (\lambda_{calibration})(I_{S_{calibration}})$$

$$C_{estimated} = (\lambda_{calibration})(I_{S_{measured}})$$

$$\lambda_{calibration} = (1.03E4)P_{Tcalibration}$$

$$P_{Tcalibration} = 20.6$$

$$\Rightarrow \lambda_{calibration} = 2.14 \times 10^5$$

Other relationships are possible and may depend on the nature of the electrochemical sensor system, environmental factors, apparatus factors, and/or sample factors.

Another example of correcting for errors in analyte concentration estimate that may arise from variations in $P_T$ is to adjust the measured current to account for variations in $P_T$. A similar analyses of the calibration curve equation shows that the measured current $I_{S_{measured}}$ may be adjusted by a factor of $$\left(\frac{P_{Tcalibration}}{P_{Tmeasured}}\right)$$

as follows:

$$C_{estimated} = (\lambda_{calibration})(I_{S_{measured}})$$

$$I_{S_{corrected}} = I_{S_{measured}}\left(\frac{P_{Tcalibration}}{P_{Tmeasured}}\right)$$

$$C_{corrected} = (\lambda_{calibration})(I_{S_{corrected}}) = (\lambda_{calibration})I_{S_{measured}}\left(\frac{P_{Tcalibration}}{P_{Tmeasured}}\right)$$

Another example of correcting for errors in analyte concentration estimate that may arise from variations in $P_T$ is to adjust the estimated analyte concentration to account for variations in $P_T$. A similar analyses of the calibration curve equation shows that the estimated concentration $C_{estimated}$ may be adjusted by a factor of $$\left(\frac{P_{Tcalibration}}{P_{Tmeasured}}\right)$$

as follows:

$$C_{estimated} = (\lambda_{calibration})(I_{S_{measured}})$$

$$C_{corrected} = (\lambda_{calibration})I_{S_{measured}}\left(\frac{P_{Tcalibration}}{P_{Tmeasured}}\right) = C_{estimated}\left(\frac{P_{Tcalibration}}{P_{Tmeasured}}\right)$$

other adjustments may be made to correct for variations in $P_T$ and that the form of the adjustment depends on apparatus factors, environmental factors, and/or sample factors that are relevant to the measurement system.

FIG. 10 illustrates a difference in calibration curves that can result from different values of $P_T$. Data points 1510 were from a system with $P_T$=6.58 s; data points 1505 were from a system with $P_T$=20.6; data points 1500 were from a system with $P_T$=44.3 s. It is clear that as the value of $P_T$ changes, sensor response changes, as reflected by the different calibration curves. Thus, if a sensor system were developed and calibrated with a particular value of $P_T$, the value of $P_T$ when the sensor was used should be substantially the same in order to maintain substantially the same sensor reading. However, if the value of $P_T$ were different when the sensor was used, then the measurement may be inaccurate. Examples of why the value of $P_T$ may be different at the time of use of a sensor include manufacturing variations in the distance between the electrodes of the conduction cell and variations in the effective mobility of the species in the sample.

FIG. 11 illustrates an example of the type of error that can arise from variations in $P_T$. In this example, the system of FIG. 2 implemented with the processes of FIG. 3 is simulated with $P_T$=20.6 s. The error in estimating analyte concentration is expressed as a percent of the value obtained with $P_T$=20.6 s. Thus, as $P_T$ decreases below 20.6 s, the estimated analyte concentration increases at a rapid rate, resulting in a falsely high estimate; as $P_T$ increases above 20.6 s, the estimated concentration decreases, resulting in a falsely low estimate. It is important to note that at small values of $P_T$, the estimation of analyte concentration is much more sensitive to variations in $P_T$ than at larger values of $P_T$. At small volumes, where the spacing between the electrodes is small, the ability to correct for variations in $P_T$ is thus of even greater value and usefulness. Likewise, in systems comprising species with high mobilities and/or high diffusion, this also can result in small values of $P_T$, again illustrating the usefulness and value of the invention in correcting for variations in $P_T$.

Figure 13A:
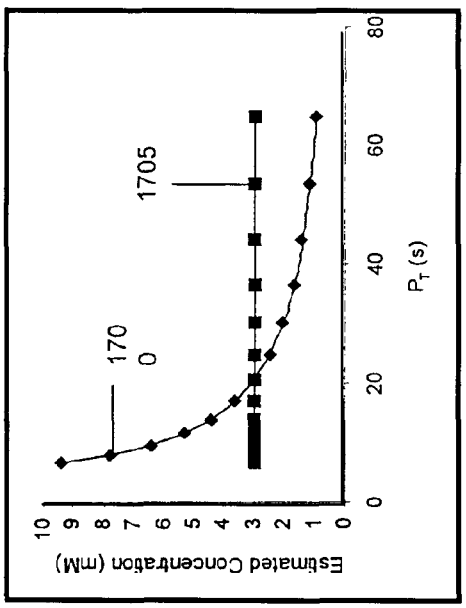
FIGS. 13A-C illustrates scenarios for correcting an estimate due to variations in $P_T$.
Figure 13C:
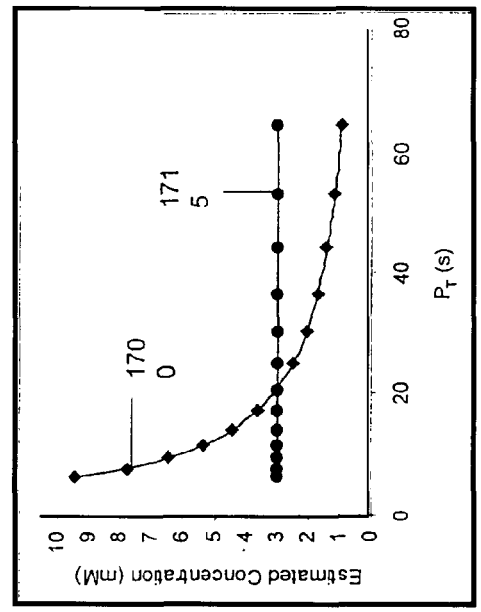
Figure 13B:
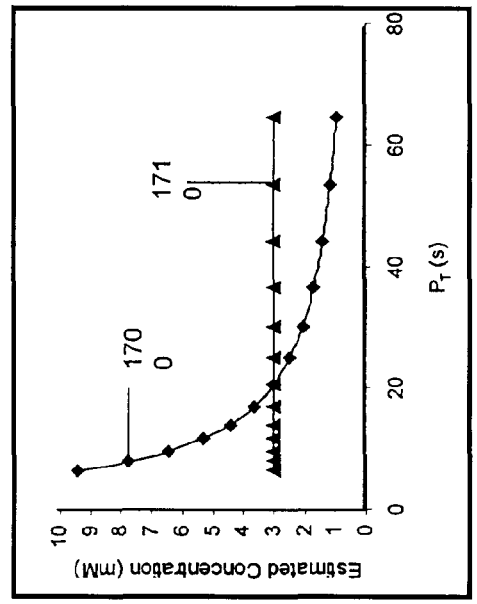

FIGS. 13A-C illustrates scenarios for correcting an estimate due to variations in $P_T$. In these examples, an analyte concentration of 3 mM is used with a system calibrated with $P_T$=20.6 s. In FIGS. 13A, 13B, and 13C, data points 1700 show how the estimated analyte concentration can vary when measurements are made with sensors with different values of $P_T$. As expected, when the value of the sensor is substantially 20.6 s, then the estimated concentration is substantially close to the correct value of 3 mM. FIG. 13A illustrates the effect of correcting the final estimated analyte concentration by accounting for variation in $P_T$. Data points 1705 are the estimated analyte concentration after a correction process was used that adjusts the estimated concentration values in data points 1700 based on the value of $P_T$ for that sensor measurement. FIG. 13B illustrates the effect of correcting the final estimated analyte concentration by adjusting the calibration curve to account for variation in $P_T$. Data points 1710 are the estimated analyte concentration after a correction process was used that adjusts the calibration curve that is used to estimate the concentration values in data points 1700 based on the value of $P_T$ for that sensor measurement. FIG. 13C illustrates the effect of correcting the final estimated analyte concentration by adjusting the measured current signal to account for variation in $P_T$. Data points 1715 are the estimated analyte concentration after a correction process was used that adjusts the measured amperometric signal that is used in estimating the concentration values in data points 1700 based on the value of $P_T$ for that sensor measurement. Thus, it is evident that embodiments of the invention are useful in reducing errors in estimating analyte concentration that can arise from variations in $P_T$.

Figures 14A, 14B, 14C:
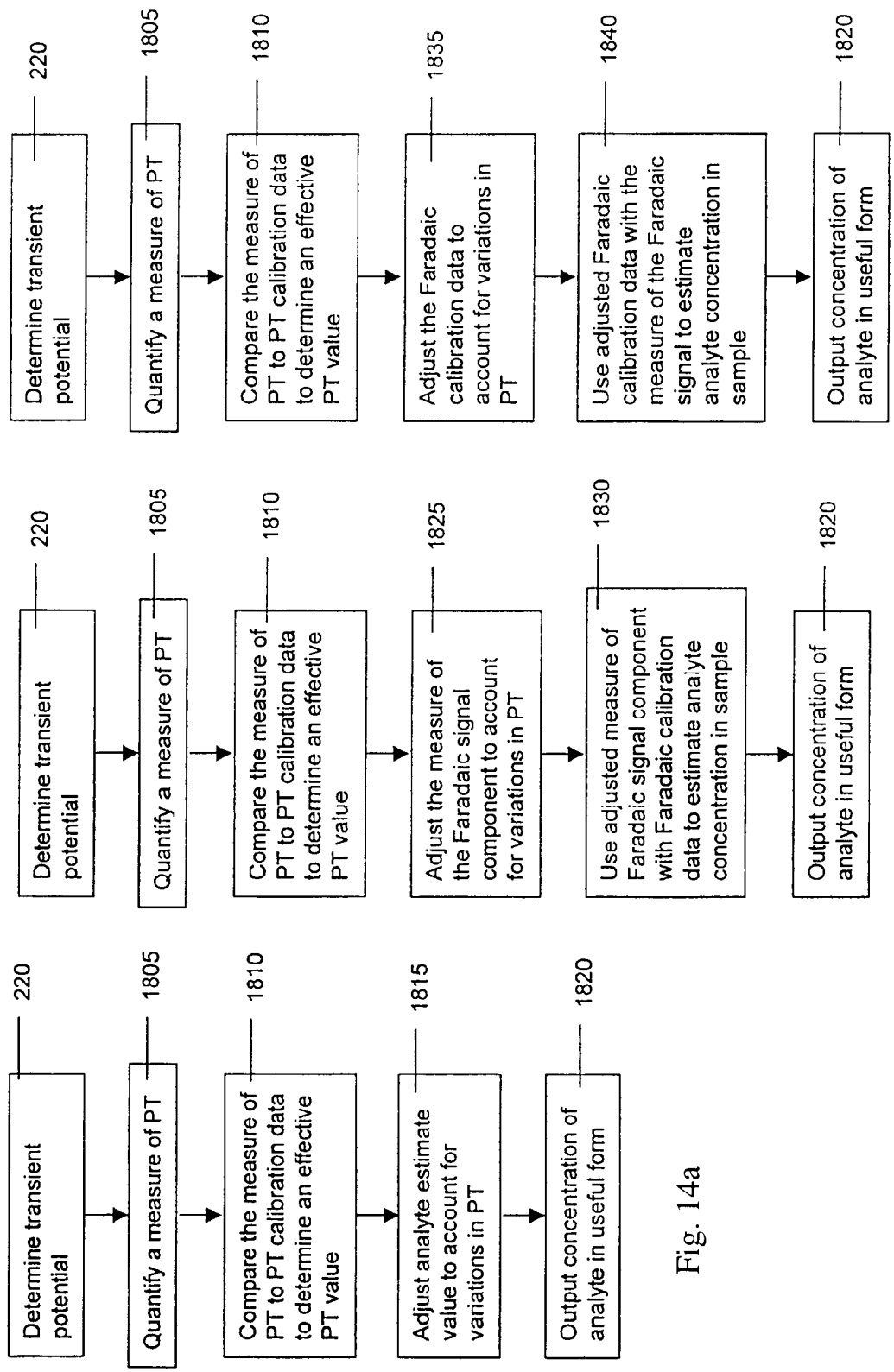
FIGS. 14A-C illustrate in flow-chart form example embodiments of the invention.

FIGS. 14A-C illustrate in flow-chart form example embodiments of the invention. As discussed in this document, there are different embodiments that can be used for the method of the invention. FIGS. 14A-C give further detail to the steps of FIG. 4 by illustrating example embodiments of step 225, step 230, and step 235 of FIG. 4.

FIG. 14A illustrates one example embodiment in which an adjustment is made to the final analyte estimate, as was illustrated by the example of FIG. 13A. In this embodiment, the transient potential is determined (step 220). Then a measure of $P_T$ is quantified (step 1805). The measure of $P_T$ is compared to calibration data to determine an effective value of $P_T$ (step 1810). The effective value of $P_T$ is used to adjust the analyte estimate to account for variations in $P_T$ (step 1815). The adjusted analyte concentration is output in a useful form (step 1820).

FIG. 14B illustrates one example embodiment in which an adjustment is made to a measure of the Faradaic signal component, as was illustrated by the example of FIG. 13B. In this embodiment, the transient potential is determined (step 220). Then a measure of $P_T$ is quantified (step 1805). The measure of $P_T$ is compared to calibration data to determine an effective value of $P_T$ (step 1810). The effective value of $P_T$ is used to adjust the measure of the Faradaic signal component to account for variations in $P_T$ (step 1825). The adjusted measure of the Faradaic signal component is used with the Faradaic calibration data to estimate the analyte concentration (step 1830). The estimate of the analyte concentration is output in a useful form (step 1820).

FIG. 14C illustrates one example embodiment in which an adjustment is made to calibration data, as was illustrated by the example of FIG. 13C. In this embodiment, the transient potential is determined (step 220). Then a measure of $P_T$ is quantified (step 1805). The measure of $P_T$ is compared to calibration data to determine an effective value of $P_T$ (step 1810). The effective value of $P_T$ is used to adjust Faradaic calibration data to account for variations in $P_T$ (step 1835). The adjusted Faradaic calibration data is used with the measure of the Faradaic signal component to estimate the analyte concentration (step 1840). The estimate of the analyte concentration is output in a useful form (step 1820).

Example 2

Enzyme Biosensor Example

In another example embodiment, the conduction-cell electrochemical sensor is operated as a biosensor. In this case, a set of chemical reactions produces an analyte to be detected by the conduction-cell electrochemical sensor. One embodiment of this is illustrated in FIG. 1 where an enzyme glucose oxidase catalyzes a reaction with glucose. In this example, glucose 500 reacts with the oxidized form of glucose oxidase, GODox 510, thereby converting the enzyme to its reduced form GODred 515 and producing gluconolactone 505. GODred 515 can react with ferricyanide, $Fe(CN)_6^{3-}$ 525 to be returned to its oxidized state GODox 510 and produce ferrocyanide, $Fe(CN)_6^{4-}$ 520. Thus, the concentration of glucose may be estimated by determining the concentration of ferrocyanide by the method and apparatus of embodiments of the invention.

The measured current can be related to the glucose concentration by a calibration curve equation. One example of such an equation is:

$$C_{estimated}^{glucose} = (\lambda_{calibration}^{glucose})(I_{S_{measured}})$$

where $C_{estimated}^{glucose}$ is the estimated glucose concentration, $\lambda_{calibration}^{glucose}$ is a proportionality constant, and $I_{S\,measured}$ is the measured current. One example of a correction factor that can be used to correct for variations in $P_T$ is to follow the process described above for a conduction-cell electrochemical sensor and develop an analogous correction equation whereby the measured $P_T$ value is used to adjust the calibration curve, the measured current, or the concentration estimate as follows:

$$C_{estimated}^{glucose} = (\lambda_{calibration}^{glucose})(I_{S\,measured})$$

$$C_{corrected}^{glucose} = (\lambda_{calibration}^{glucose}) I_{S\,measured} \left( \frac{P_{Tcalibration}^{glucose}}{P_{Tmeasured}^{glucose}} \right) = C_{estimated}^{glucose} \left( \frac{P_{Tcalibration}^{glucose}}{P_{Tmeasured}^{glucose}} \right)$$

where $P_{T\,calibration}^{glucose}$ is the value of $P_T$ obtained when determining a calibration curve for a conduction-cell biosensor used to estimate glucose concentrations, $P_{T\,measured}^{glucose}$ is the value of $P_T$ obtained when measuring glucose in a conduction-cell biosensor, and $C_{corrected}^{glucose}$ is the corrected glucose concentration.

Example 3

Example Embodiments of Transducer Control Apparatus

Figure 15:
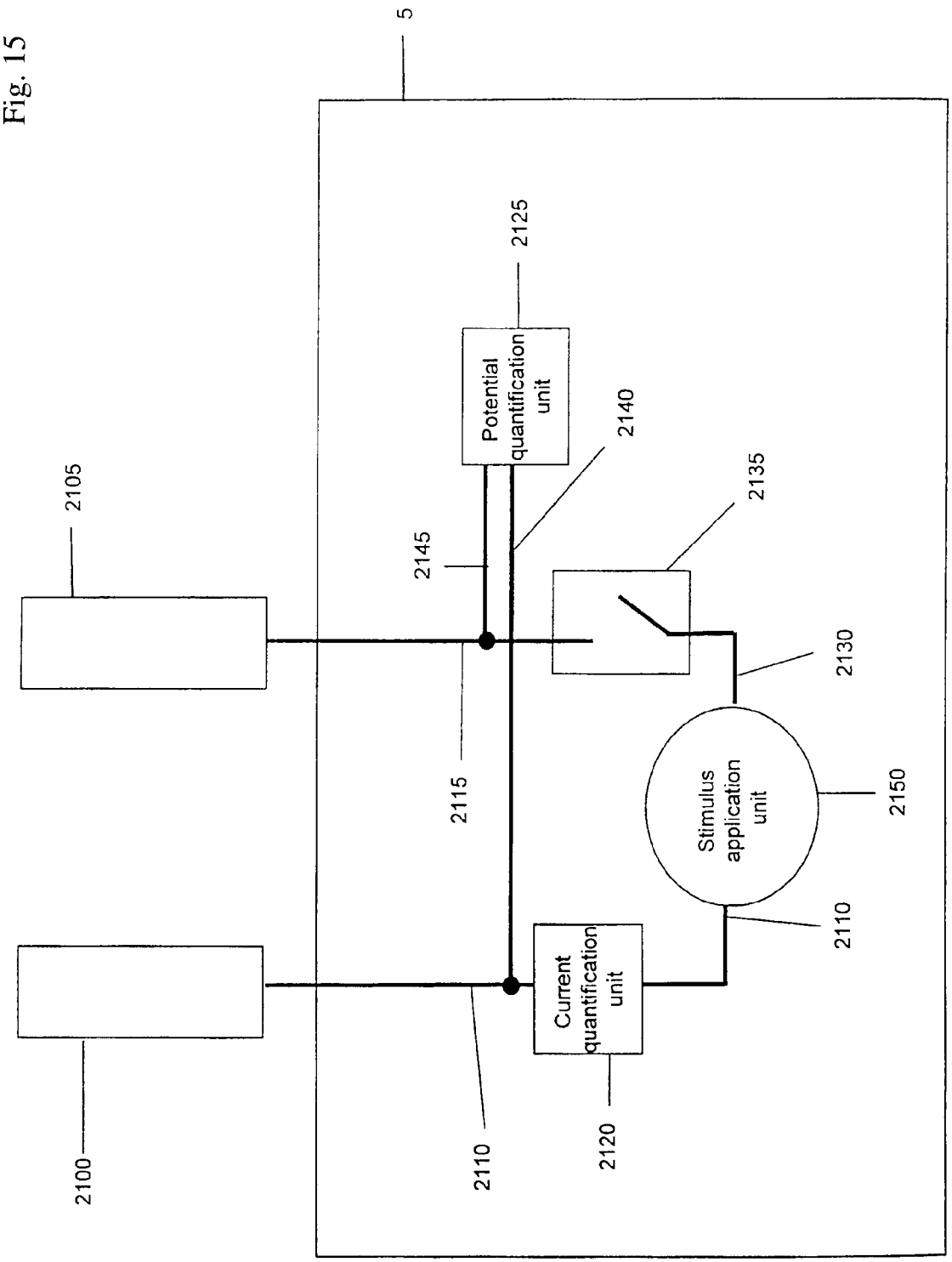
FIG. 15 illustrates a schematic for one example embodiment of the Transducer control apparatus.

One example embodiment of the transducer control apparatus 5 in FIG. 2 is discussed. FIG. 15 illustrates a schematic for one example embodiment of the Transducer control apparatus 5. Two electrodes 2100 and 2105 are coupled to the TCS 5 by substantially conductive paths 2110 and 2115. A stimulus application unit 2150 can apply a potential difference between substantially conductive paths 2110 and 2130. The stimulus application unit 2150 can vary the potential difference in time. A current quantification unit 2120 monitors the current that flows along lead 2110. One of ordinary skill in the art will recognize that the current flowing along lead 2110 is substantially the same as the current flowing along leads 2115 and 2130. The current quantification unit 2120 may be connected to lead 2115 or 2130 instead of to lead 2110. This embodiment does not limit the invention. A switch unit 2135 allows the ability to electrically connect or disconnect lead 2130 to lead 2115. This switch unit enables the TCA 5 to force the current flow to be substantially zero amps. One of ordinary skill will recognize that other methods are possible to force current flow to be substantially zero amps, such as switching to a high-impedance circuit element. Examples of a switch unit 2135 include a solid-state switch such as a MOSFET switch (e.g. AD417 chip from Analog Devices); an electro-mechanical switch; and a mechanical switch.

The switch unit 2135 may be connected in a manner so as to enable the short-circuiting and/or open-circuiting of lead 2110 instead. One of ordinary skill in the art will recognize that there are different placement and operational options for changing between one operating mode where current flow is not substantially impeded to another operating mode where current flow is substantially impeded. A potential quantification unit 2125 monitors the potential difference between lead 2115 and lead 2110. This potential difference is related to the potential difference between electrode 2105 and 2100. In a preferred embodiment, the potential at lead 2115 is substantially equal to the potential at electrode 2105 and the potential at lead 2110 is substantially equal to the potential at electrode 2100.

When the TCA 5 is operating in amperometric mode, switch 2135 is in a close-circuit operation mode, a potential difference is applied by the stimulus application unit 2150 and the resulting current is monitored by the current quantification unit 2120 and the potential is monitored by the potential quantification unit 2125. When the system switches to a potentiometric operation mode, switch 2135 changes to an open-circuit—or high impedance—operation mode, the current quantification unit 2120 monitors the current flow—which is expected to be substantially zero amps—and the potential quantification unit monitors the potential difference—which is expected to follow a relaxation decay over time.

A more specific example embodiment for the TCA 5 is illustrated in FIG. 16. Circuit element 2220 represents a substantially conductive path to a reference potential, such as ground. All thick solid lines represent substantially electrically conductive paths ("leads"). The stimulus potential is applied between lead 2215 and ground lead 2220. When switching unit 2230 is in a close-circuit mode, lead 2225 and lead 2250 are at substantially the same potential and amplifier 2200 maintains substantially the same potential at lead 2250 as is present at lead 2215. One example of such an amplifier 2200 is an operational amplifier ("op-amp"). Lead 2250 is connected to electrode 2240. A second amplifier 2205 maintains one connection to ground lead 2220 and another connection via lead 2265 to electrode 2245. A feedback resistor 2255 connects lead 2265 to lead 2260. The potential difference that exists between lead 2260 and ground lead 2220 is related to the current that flows through the electrochemical cell. Another amplifier monitors the difference between lead 2250 and lead 2265, and thereby monitors substantially the same potential that exists between electrode 2240 and electrode 2245. One example of such an amplifier 2210 is a differential amplifier. Another example is an instrumentation amplifier. The potential difference between lead 2270 and ground lead 2220 is related to the potential difference between lead 2250 and lead 2265. When switching unit 2230 is in open-circuit operation, the amplifier 2200 ensures that substantially zero current flows along lead 2250 and electrode 2240. Thus, the potential at lead 2260 is substantially the same as the potential at the ground lead 2220. the potential between the electrodes 2240 and 2245 is monitored by amplifier 2210 and manifested by a potential difference between lead 2270 and ground lead 2220.

Example 4

Another Metric for Quantifying $P_T$

Figure 17:
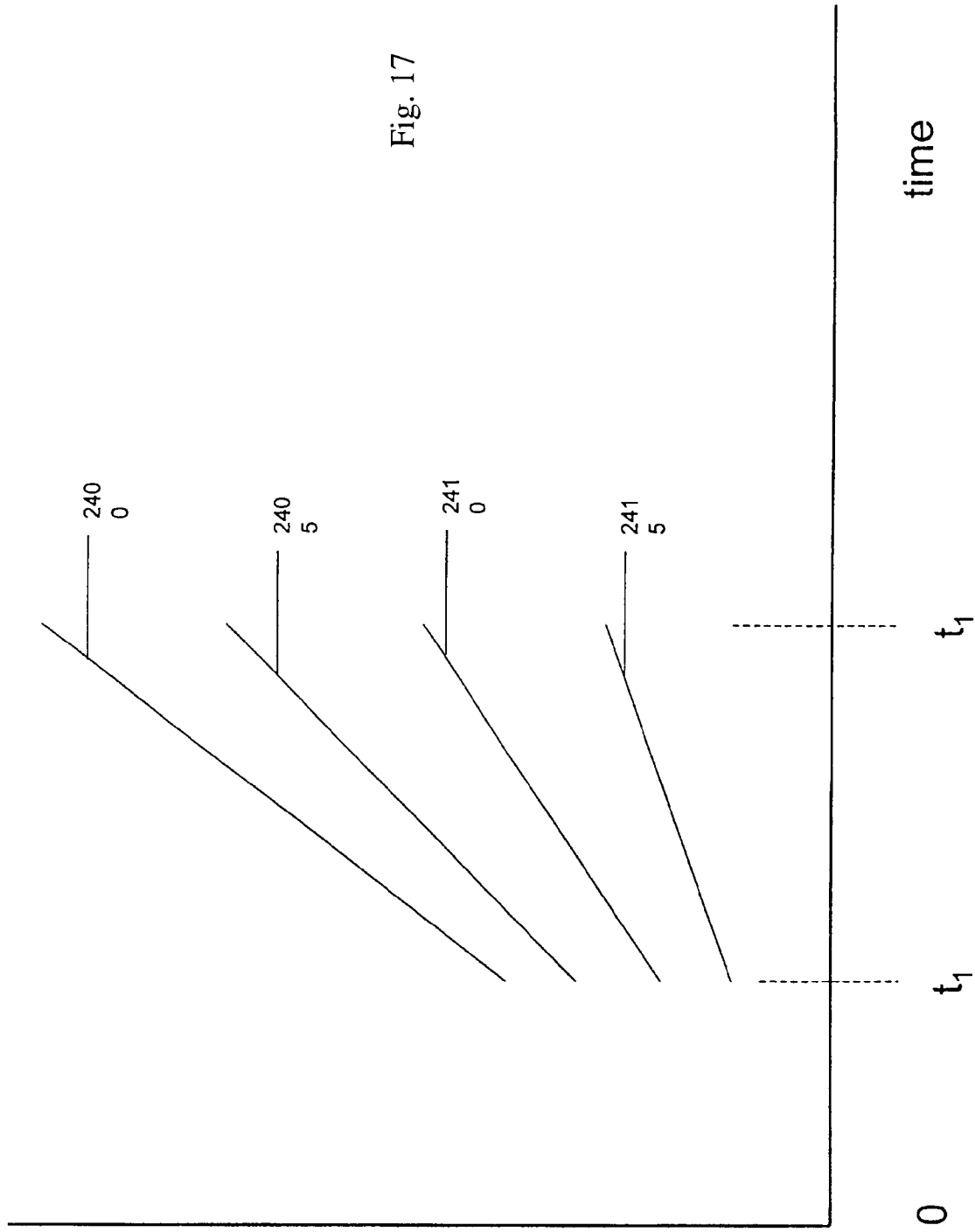
FIG. 17 illustrates a schematic representation of the potentiometric relaxation signal as a function of time for different values of $P_T$.

As mentioned above, another example embodiment for extracting a measure of $P_T$ is to determine a measure of the rate of relaxation of the potentiometric signal by determining a slope of $1/V^2$ versus time during a particular period of time, as illustrated by a schematic in FIG. 17. FIG. 17 illustrates a schematic representation of the potentiometric relaxation signal as a function of time for different values of $P_T$. In this example, the potentiometric relaxation was started at a time t=0 by, for example, substantially open-circuiting the electrochemical cell. The y-axis plots the function of $1/V^2$, where V is the measured potential, during a period of time from t1 until t2. Data traces 2400, 2405, 2410, and 2415 represent the relaxation signals from measurements with different values of $P_T$. In this example, the value of $P_T$ associated with data 2400 is smaller than the value of $P_T$ associated with data 2405, which is in turn smaller than the value of $P_T$ associated with data 2410, which is in turn smaller than the value of $P_T$ associated with data 2415. In this example, it is clear that there is a substantially linear relationship between $1/V^2$ and the time. Thus, a measure of the rate of relaxation may be obtained by determining a slope of this data in a period of time, for example between time $t_1$ and time $t_2$. A slope may be calculated by well-established means in linear algebra, including, but not limited to, a least squares method.

Figure 18:
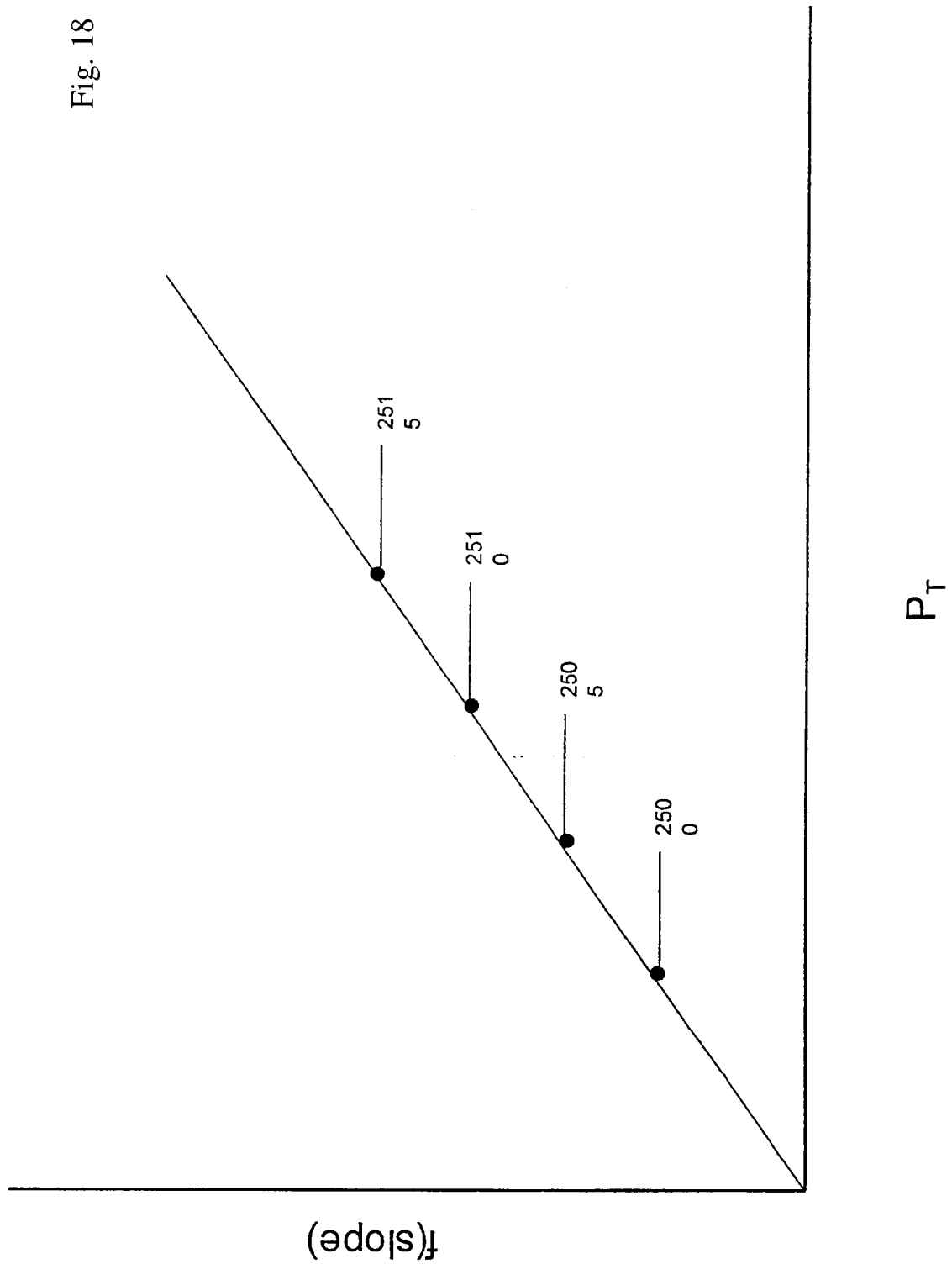
FIG. 18 illustrates in schematic form one example of quantifying a measure of $P_T$ from the measured data.

FIG. 18 illustrates in schematic form one example of quantifying a measure of $P_T$ from the measured data. A calibration curve can be constructed that relates $P_T$ to a measure of $P_T$. The example illustrated by the schematic of FIG. 18 shows that some function of the slope of $1/V2$ versus time—depicted as f(slope) on the y-axis—can be used as a measure of $P_T$. One example embodiment of such a function is:

$$f(\text{slope}) = \frac{1}{\sqrt{\text{slope}}}$$

where slope is the slope of the plot of $1/V2$ versus time during a portion of time. In FIG. 18, point 2500 corresponds to data trace 2400 in FIG. 17; point 2505 corresponds to data trace 2405 in FIG. 17; point 2510 corresponds to data trace 2410 in FIG. 17; point 2515 corresponds to data trace 2415 in FIG. 17. Thus, a measure of $P_T$ can be computed from the measured potentiometric data. Once the measure of $P_T$ is determined, this value can be used as discussed above to adjust various quantities to obtain a more accurate estimate of analyte concentration.

Example 5

Performing Correction with Transient System

The invention may also be used in situations where the system has not reached steady state; such a state is also commonly known as a transient state. Examples of a system in transient state include, but are not limited to, a response signal whose characteristics vary with time, a concentration profile in a sample which substantially varies with time, and a chemical reaction which has not reached equilibrium.

One difference between a steady-state system and a transient system is that signals generated by a steady-state system are expected to contain significant information about a distance term related to separation distance between the electrodes and/or information about a transport term related to the transport properties of the sample (for example, an effective diffusion coefficient or a mobility term). For example, as discussed above $P_T$ can be described in part by an effective electrode separation term h as well as other terms related to the transport properties of the sample, such as a diffusion term D, a drift speed s, and/or a mobility term U. Signals generated by a transient system are not expected to contain significant information about a distance term related to a separation distance between electrodes, but would be expected to contain information related to the transport properties of the sample. However, even in transient systems, there may be significant information related to an effective distance term, though that distance term may not be directly related to a geometric separation distance between two electrodes.

In a steady state system, there is substantial transfer of chemical information from one electrode to the other through the sample by the concentration gradients of chemical species in the vicinity of one electrode being perturbed by the processes occurring at another electrode. One example of this is when reaction products of one electrode reach the other electrode. In a transient system, there is not substantial chemical information transferred through the sample from one electrode to the other. For example, reaction products from one electrode may have not substantially reached the other electrode, so it is expected that there is little information in the signal about a measure of the distance between the electrodes. There is, however, expected to be information about transport of analyte in the sample, for example a transport term related to a diffusion term, a mobility term or an effective path length term. One example of such a path length term is an effective distance term related to transport of analyte in a sample comprising substances such as red blood cells or other bodies. Bodies in a sample can affect the transport of analyte in a sample, and therefore an ability to correct for such transport-related variations in transient systems would be useful and beneficial for increasing the accuracy and/or precision of a sensor system.

FIG. 19 illustrates in schematic form examples of amperometric signals for a transient system. In this example, three current traces are shown which correspond to different glucose concentrations. Trace 2900 is the lowest concentration, trace 2905 is the intermediate concentration and trace 2910 is the highest concentration. The signals are divided into six regions in time as shown. In this example, the sample was introduced into the sample chamber at t=0, at which point the potential was stepped up to a level sufficient for a substantially diffusion limited current to be generated. The increase in current from t=0 to t=t1 may be ascribed predominantly to capacitative double layer charging. The decrease in current from t1 to t2 may be ascribed predominantly to stabilization of the double layer. The increase in current between t2 and t3 may be ascribed predominantly to the increase of reduced mediator—ferrocyanide in this example—from the progress of the chemical reaction with an analyte in the sample (in this example the chemical reaction is the enzyme reaction with glucose). The current reaches a local maximum at approximately time t3, at which point the progress of the enzyme reaction is balanced by the diffusion processed governing transport of the electroactive species—the mediator in this example—to the electrodes. resulting in a fall in current after time t3. The falling current in some cases continues to decrease is there is an apparent semi-infinite diffusion profile during the course of the measurement.

Since the current signal continues to fall, it may be said that this system is in a transient state. The transient signal can be analyzed and quantified to determine a measure of the analyte concentration, and a steady state current is not necessary for the invention to be used. One example of the type of analysis that can be performed with a transient current is related to the Cottrell equation. Of course, the Cottrell equation applies to a particular set of measurement conditions and other equations can be used to describe a system depending on the measurement conditions. One example equation that can be used is to compute a square-root of a slope of $1/I^2$ during a portion of time as a measure of the glucose concentration. In the example schematic of FIG. 19, a portion of time after the current substantially is independent of the enzyme reaction (for example, after a peak in the current at approximately time t3) such as the time between t4 and t5 can be used for such quantification. In this example, an equation based on the Cottrell equation can be used to describe the current of a transient system as follows:

$$I = nFAC\sqrt{\frac{D}{\pi(t-t_0)}}$$

$$\frac{1}{I^2} = \left(\frac{\pi}{(nFA)^2}\right)\frac{1}{DC^2}(t-t_0)$$

$$\frac{1}{I^2} = \alpha t + \beta$$

$$\alpha = \frac{\pi}{(nFA)^2 DC^2}$$

$$\beta = -\left(\frac{\pi}{(nFA)^2}\right)\frac{1}{DC^2}t_0$$

where $t_0$ is a reference time, and the other symbols retain their usual meanings. The slope, given by $\alpha$, and D can be used to determine a measure of concentration, C. For a system that has a known value for D, it is therefore possible to quantify the concentration by determining the slope $\alpha$, for example by an estimation equation such as:

$$C = \sqrt{\frac{\pi}{(nFA)^2 D\alpha}}$$

A problem arises if sample, apparatus, and/or environmental factors vary and cause an unknown change in the apparent value of D. In such a case, the estimate of concentration, C, would subsequently vary in an unknown manner, resulting in decreased accuracy and/or precision.

With such a transient system, the apparatus can be switched to potentiometric mode to monitor a potentiometric relaxation to determine a measure of the variations in transport and/or path length related properties of the system. In this example, a potentiometric relaxation would be used to determine an effective measure of D, which would be used to estimate the concentration. Thus, the method and apparatus of the invention does not require a steady-state or near-steady-state system; instead, the method and apparatus of the invention may be used with a transient system.

One factor that can influence the transient or steady-state nature of the system is the geometry of the electrochemical cell. One example of such a geometric factor is the effective distance between the electrodes. The smaller the effective distance, the less time it generally takes for the system to reach steady state. In this example, steady state can be defined as when the amperometric signal reaches a near steady-state value. The larger the effective distance between the electrodes, the more time it generally takes to reach steady state. Thus, whether the system is in steady-state or transient mode when the operation is switched from amperometric to potentiometric can depend on the both the effective distance between the electrodes and the time at which the mode of operation changes. For example, if the effective separation is large enough that steady state is not substantially achieved within a given period of time, then the mode of operation may be switched in to potentiometric mode while in the transient state. One useful benefit of using the method and apparatus of the invention with a transient system is that a measurement may be made in less time. As in the steady state measurement in Example 4, for transient measurements there is a substantially linear relationship between $1/V^2$ and the time. Thus, a measure of the rate of relaxation may be obtained by determining a slope of this data in a period of time, for example between time $t_1$ and time $t_2$. A slope may be calculated by well-established means in linear algebra, including, but not limited to, a least squares method. Other relationships may exist for different electrode geometries.

Figure 20B:
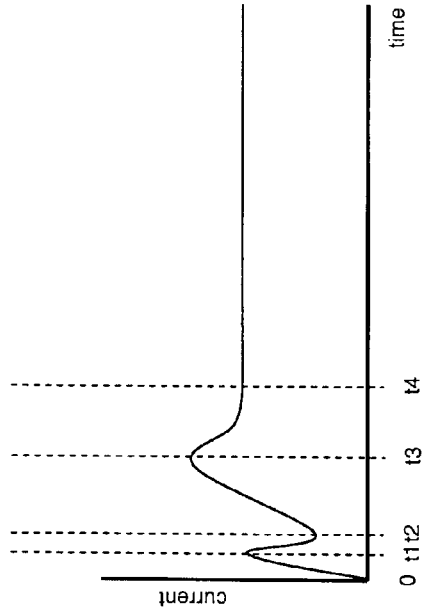
FIGS. 20A-C illustrate in schematic form several example amperometric signals that may be generated by conduction-cell based biosensor systems.
Figure 20C:
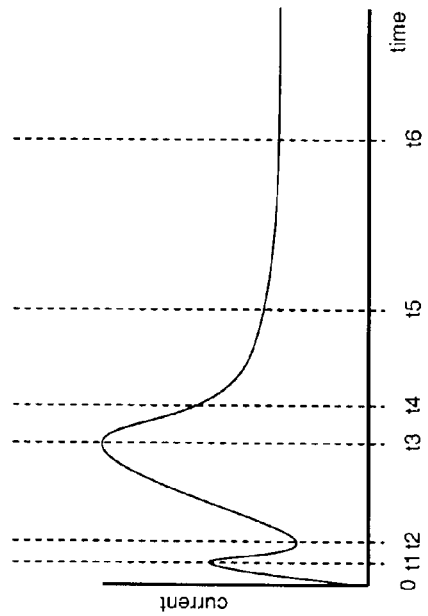
Figure 20A:
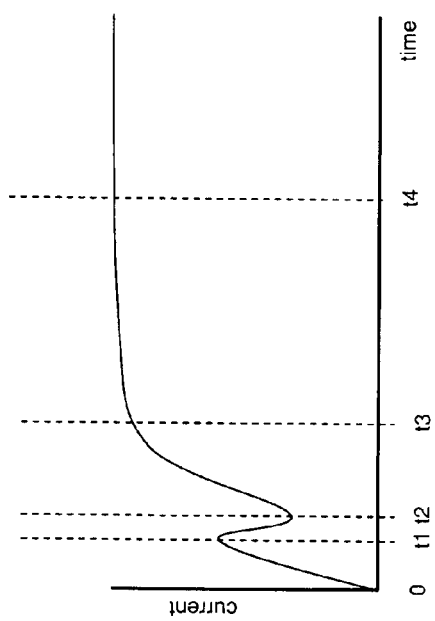
Figure 21A:
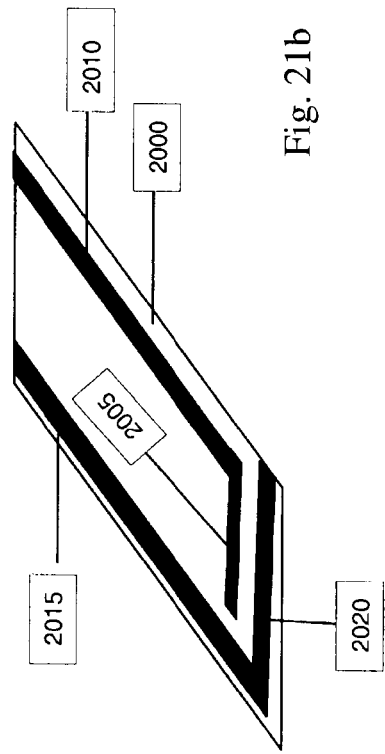
FIGS. 21A-D illustrate in schematic form several example arrangements of substantially coplanar electrodes.
Figure 21B:
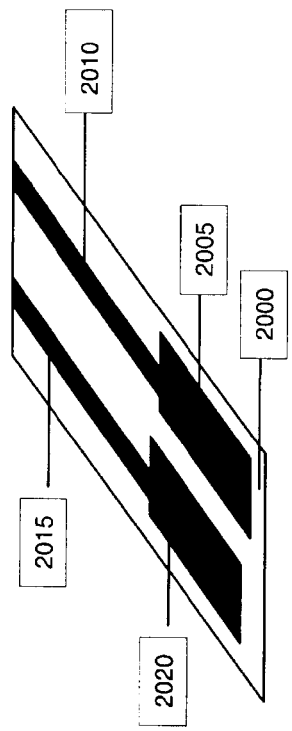
Figure 21C:
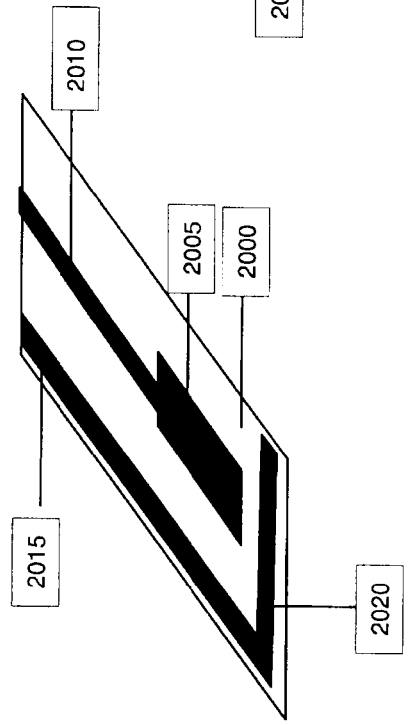
Figure 21D:
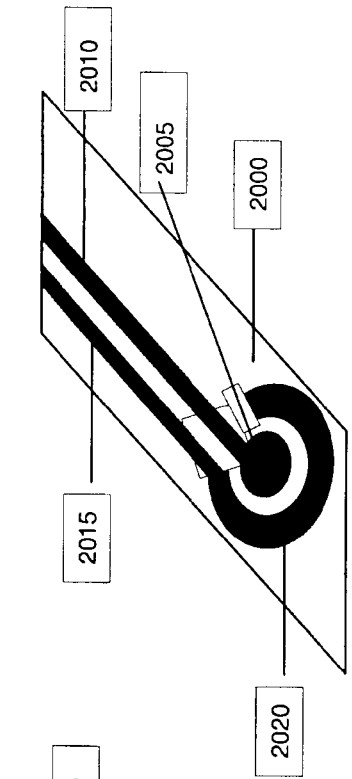

FIGS. 20A-C illustrate in schematic form several example amperometric signals that may be generated by conduction-cell based biosensor systems. FIG. 20A illustrates an example scenario where the effective separation distance between the electrodes is large enough to allow at least one portion of the response signal to follow a transient form that may be described by a relaxation related to the Cottrell equation. This figure is similar to the example illustrated in FIG. 19 except that the signal is shown to deviate from a substantially semi-infinite relaxation that may be substantially related to a Cottrell-type relaxation (between t4 and t5), go through a transition region (between t5 and t6) and ultimately reach a substantial steady-state value (after t6). Thus, various equations and/or expressions can be used to describe the signal response during these different regions. FIG. 20B illustrates an example scenario where the effective separation distance between the electrodes is large enough to allow a diffusion gradient relaxation (between t3 and t4) but small enough to reach a substantially steady-state current value (after t4) without significantly experiencing a substantially semi-infinite (e.g. Cottrell-like) relaxation. FIG. 20C illustrates an example scenario where the effective separation distance between the electrodes is small enough such that a substantially steady-state current is reached (after t4) without experiencing a significant diffusion relaxation. These figures are example embodiments of signals that may be generated by enzyme-based biosensors and do not limit the invention. One of ordinary skill in the art will recognize that other signal responses are possible and that the form of the signal depends on many factors, including but not limited to apparatus factors, sample factors, and environmental factors.

Another geometric factor that can influence the transient or steady-state nature of the system is the orientation of the electrodes. A traditional orientation for conduction cells has been for cells comprised of two substantially parallel electrodes facing each other, usually of approximately the same area, as illustrated by the example in FIGS. 7A-C. The principal reason for such a geometry has been that this is a convenient electrode orientation for determining the cell constant $K_{cell}$. However, the method and apparatus of the invention allows other geometries to be used in a conduction-cell operation. Examples include cells comprised of substantially coplanar electrodes and/or substantially concentric electrodes (examples of which are shown in FIGS. 21A-D).

FIGS. 21A-D illustrate in schematic form several example arrangements of substantially coplanar electrodes. In these example illustrations, the arrangements are comprised of a substantially non-conducting substrate 2000, at least two electrodes 2005 and 2020, and at least two substantially conducting leads 2010 and 2015. The substantially conducting leads (2010 and 2015) need not be separate material from the electrodes (2005 and 2020). These illustrations are provided as example embodiments and do not limit the invention. One of ordinary skill in the art will recognize that other embodiments are possible, including but not limited to different shapes, different orientations, and/or different alignments of electrodes.

Other factors that can influence the transient or steady state nature of the system are sample properties, for example, diffusion, mobility, path length, and/or hematocrit level. Properties of the sample itself can alter the rate of transport of species, thereby altering the time needed to achieve substantially a steady-state system.

The invention therefore provides a method and apparatus for determining a measure of PT that does not require the system to be substantially in steady-state, but can be implemented on a transient system. This has the useful benefit of substantially reducing the measurement time, since a user does not need to wait until substantial steady state has been achieved. Another useful benefit is that different cell geometries can be used, including, for example, parallel-facing, coplanar, and/or concentric arrangements of electrodes, since such geometries may not quickly and easily achieve substantial steady-state. Furthermore, since the invention can be used with transient systems as well, there is no requirement that the electrodes must be sufficiently close to each other to achieve a substantial steady-state operation. Electrochemical cells manufactured at these larger scales are known to be easier, and hence less costly, to make.

It will be apparent to those skilled in the art that additional various modifications and variations can be made without departing from the scope or spirit of the invention.

Other embodiments of the invention will be apparent to those skilled in the art from consideration of the specification and practice of the invention disclosed herein.

REFERENCES CITED

Schmidt-Weinmar, von H. G. "Ueber die Polarisation einer symmetrischen Redoxzelle mit kleinem Elektrodenabstand: Eine Methode zur Bestimmung der Ionenbeweglichkeit". Berichte der Bunsengesellschaft. Vol 71, No. 1. 1967.

Brett, C M A and A. M. O. Brett. "Electrochemistry: Principles, Methods, and Applications", 1st ed. Oxford University Press, 1993.

MacInnes, D. A. "The Principles of Electrochemistry". Reinhold Publishing Corp. New York. 1939.

Crow, D. R. "Principles and Applications of Electrochemistry". 4th ed. Stanley Thornes Publishers. Cheltenham, UK. 1998.

Atkins, P. "Physical Chemistry". 6th ed. Freeman. New York. 1999.

Lathi, B. P. "Linear Systems and Signals", Berkeley-Cambridge Press, Carmichael, Calif. 1992.

What is claimed is:

1. A method for increasing accuracy of a determination of an analyte in a sample, comprising the steps of:
   (a) applying the sample to an electrochemical test strip;
   (b) applying a potential signal to the sample in the electrochemical test strip to result in a current signal that is indicative of the amount of analyte in the sample;
   (c) ceasing application of the potential signal and determining a transient potential;
   (d) determining from the transient potential a correction factor for the effective transport parameter ($P_T$) or the electrode area (A) or both the effective transport parameter ($P_T$) or the electrode area (A), and
   (e) applying the correction factor(s) determined in (d) to arrive at a final determination of the analyte in the sample, said final determination of the analyte in the sample being more accurate than an estimated analyte value derivable from the current signal without application of correction factor(s).

2. The method of claim 1, wherein a measure of $P_T$ is determined and compared to a calibration value of $P_T$, and wherein an estimated analyte value is determined from the current signal, and then is adjusted to account for differences between the measured $P_T$ and the calibration value of $P_T$ to arrive at the final determination of analyte.

3. The method of claim 1, wherein a measure of $P_T$ is determined and compared to a calibration value of $P_T$, and the current signal is adjusted to account for differences between the measured $P_T$ and the calibration value of $P_T$, and the final determination of analyte is calculated from the adjusted current signal.

4. The method of claim 1, wherein a measure of $P_T$ is determined and compared to a calibration value of $P_T$, and Faradaic calibration data is adjusted to the account for differences between the measured $P_T$ and the calibration value of $P_T$, the adjusted Faradaic calibration data is applied to the current signal to produce a calibrated current signal, and a final determination of analyte is calculated from the calibrated current signal.

5. The method of claim 1, wherein the electrochemical test strip comprises reagents for determination of glucose in a sample.

6. The method of claim 5, wherein a measure of $P_T$ is determined and compared to a calibration value of $P_T$, and wherein an estimated analyte value is determined from the current signal, and then is adjusted to account for differences between the measured $P_T$ and the calibration value of $P_T$ to arrive at the final determination of analyte.

7. The method of claim 5, wherein a measure of $P_T$ is determined and compared to a calibration value of $P_T$, and the current signal is adjusted to account for differences between the measured $P_T$ and the calibration value of $P_T$, and the final determination of analyte is calculated from the adjusted current signal.

8. The method of claim 5, wherein a measure of $P_T$ is determined and compared to a calibration value of $P_T$, and Faradaic calibration data is adjusted to the account for differences between the measured $P_T$ and the calibration value of $P_T$, the adjusted Faradaic calibration data is applied to the current signal to produce a calibrated current signal, and a final determination of analyte is calculated from the calibrated current signal.

9. The method of claim 1, wherein the electrochemical test strip comprises facing working and counter electrodes.

10. The method of claim 9, wherein a measure of $P_T$ is determined and compared to a calibration value of $P_T$, and wherein an estimated analyte value is determined from the current signal, and then is adjusted to account for differences between the measured $P_T$ and the calibration value of $P_T$ to arrive at the final determination of analyte.

11. The method of claim 10, wherein a measure of $P_T$ is determined and compared to a calibration value of $P_T$, and Faradaic calibration data is adjusted to the account for differences between the measured $P_T$ and the calibration value of $P_T$, the adjusted Faradaic calibration data is applied to the current signal to produce a calibrated current signal, and a final determination of analyte is calculated from the calibrated current signal.

12. The method of claim 9, wherein a measure of $P_T$ is determined and compared to a calibration value of $P_T$, and the current signal is adjusted to account for differences between the measured $P_T$ and the calibration value of $P_T$, and the final determination of analyte is calculated from the adjusted current signal.

13. The method of claim 1, wherein the electrochemical test strip comprises side-by-side electrodes.

14. The method of claim 13, wherein a measure of $P_T$ is determined and compared to a calibration value of $P_T$, and wherein an estimated analyte value is determined from the current signal, and then is adjusted to account for differences between the measured $P_T$ and the calibration value of $P_T$ to arrive at the final determination of analyte.

15. The method of claim 13, wherein a measure of $P_T$ is determined and compared to a calibration value of $P_T$, and the current signal is adjusted to account for differences between the measured $P_T$ and the calibration value of $P_T$, and the final determination of analyte is calculated from the adjusted current signal.

16. The method of claim 13, wherein a measure of $P_T$ is determined and compared to a calibration value of $P_T$, and Faradaic calibration data is adjusted to the account for differences between the measured $P_T$ and the calibration value of $P_T$, the adjusted Faradaic calibration data is applied to the current signal to produce a calibrated current signal, and a final determination of analyte is calculated from the calibrated current signal.

17. The apparatus of claim 13, wherein the circuitry of (c) determines a measure of $P_T$ and compares it to a calibration value of $P_T$,
the apparatus further comprises data storage for storing Faradaic calibration data;
the circuitry of (d) adjusts the stored Faradaic calibration to the account for differences between the measured $P_T$ and the calibration value of $P_T$, and
the apparatus further comprises circuitry for applying the adjusted Faradaic calibration data to the current signal to produce a calibrated current signal, and for making a final determination of analyte from the calibrated current signal.

18. An apparatus for determining an analyte in a sample with increased accuracy when the apparatus is operatively connected to an electrochemical test strip specific for the analyte, said apparatus comprising:
(a) circuitry for applying a potential signal to the sample in the electrochemical test strip to result in a current signal that is indicative of the amount of analyte in the sample;
(b) circuitry for ceasing application of the potential signal and determining a transient potential;
(c) circuitry for determining from the transient potential a correction factor for the effective transport parameter ($P_T$) or the electrode area (A) or both the effective transport parameter ($P_T$) or the electrode area (A), and
(d) circuitry for applying the correction factor(s) determined in (c) to arrive at a final determination of the analyte in the sample, said final determination of the analyte in the sample being more accurate than an estimated analyte value derivable from the current signal without application of correction factor(s).

19. The apparatus of claim 18, wherein the circuitry of (c) determines a measure of $P_T$ and compares this measure to a calibration value of $P_T$,
wherein the apparatus further comprises circuitry for determining an estimated analyte value from the current signal, and
wherein the circuitry of (d) adjusts the estimated analyte value to account for differences between the measured $P_T$ and the calibration value of $P_T$ to arrive at the final determination of analyte.

20. The apparatus of claim 18, wherein a measure of $P_T$ is determined and compares this value to a calibration value of $P_T$, and circuitry of step (d) adjusts the current signal to account for differences between the measured $P_T$ and the calibration value of $P_T$, and
wherein the apparatus further comprises circuitry for making the final determination of analyte from the adjusted current signal.

* * * * *